(12) United States Patent
Yoelin

(10) Patent No.: US 11,878,051 B2
(45) Date of Patent: *Jan. 23, 2024

(54) REDUCING OR INHIBITING OCULAR DAMAGE BY HYALURONIDASE ADMINISTRATION

(71) Applicant: Med Progress, LLC, Newport Beach, CA (US)

(72) Inventor: Steve Yoelin, Newport Beach, CA (US)

(73) Assignee: Med Progress, LLC, Newport Beach, CA (US)

( * ) Notice: Subject to any disclaimer, the term of this patent is extended or adjusted under 35 U.S.C. 154(b) by 76 days.

This patent is subject to a terminal disclaimer.

(21) Appl. No.: 17/221,750

(22) Filed: Apr. 2, 2021

(65) Prior Publication Data

US 2021/0308234 A1    Oct. 7, 2021

Related U.S. Application Data

(60) Provisional application No. 63/004,444, filed on Apr. 2, 2020.

(51) Int. Cl.
*A61K 38/47* (2006.01)
*A61P 27/02* (2006.01)
*A61K 9/00* (2006.01)

(52) U.S. Cl.
CPC .............. *A61K 38/47* (2013.01); *A61P 27/02* (2018.01); *A61K 9/0048* (2013.01); *C12Y 302/01035* (2013.01)

(58) Field of Classification Search
CPC .. A61K 31/167; A61K 31/196; A61K 31/245; A61K 31/381; A61K 31/445; A61K 31/26; A61K 31/47; A61K 31/5375; A61K 38/47; A61K 9/0048; A61K 9/0019; A61P 27/02; A61P 9/10
See application file for complete search history.

(56) References Cited

U.S. PATENT DOCUMENTS

| 4,820,516 | A | 4/1989 | Sawyer et al. |
| 2005/0281861 | A1* | 12/2005 | Hughes ................. A61K 47/34 424/145.1 |
| 2009/0311237 | A1 | 12/2009 | Frost |
| 2012/0101033 | A1 | 4/2012 | Shantha et al. |
| 2018/0028357 | A1 | 2/2018 | Prausnitz et al. |
| 2020/0330274 | A1 | 10/2020 | Junger et al. |

OTHER PUBLICATIONS

DeLorenzi, Claudio. Discussion: Assessing Retrobulbar Hyaluronidase as a Treatment for Filler-Induced Blindness in a Cadaver Model. American Society of Plastic Surgeons. Plastic and Reconstructive Surgery. Published Mar. 2019. (Year: 2019).*
Beleznay, et al., Update on Avoiding and Treating Blindness From Fillers: A Recent Review of the World Literature, Aesthetic Surgery Journal 39(6): 662-674 (2019).
Buhren, et al., Hyaluronidase: From Clinical Applications to Molecular and Cellular Mechanisms, Eur. J. Med. Res. 21(5): 1-7 (2016).
Cavallini, et al., The Role of Hyaluronidase in the Treatment of Complications From Hyaluronic Acid Dermal Fillers, Aesthetic Surgery Journal 33(8): 1167-1174 (2013).
Cybulska, How to spot dermal filler complications and what to do about it?, Dec. 18, 2015, https://safetyinbeauty.com/how-to-spot-dermal-filler-complications-and-what-to-do-about-it-by-dr-beata-cybulska/ (2015).
Fisher, et al., A Novel Technique to Characterize Key Fluid Mechanic Properties of the Suprachoroidal Injection Procedure in an In Vivo Model, Poster C0234, 2018 ARVO Annual Meeting Apr. 29-May 3, 2018).
Hilton, et al., Hyaluronidase injection for the treatment of eyelid edema: a retrospective analysis of 20 patients, European Journal of Medical Research 2014, 19:30 http://www.eurjmedres.com/content/19/1/30 (2014).
Hiwang, et al., Role of Retrobulbar Hyaluronidase in Filler-Associated Blindness: Evaluation of Fundus Perfusion and Electroretinogram Readings in an Animal Model, Ophthal. Plast. Reconstr. Surg., 35(1): 33-37 (2019).
Jung, Hyaluronidase: An overview of its properties, applications, and side effects, Archives of Plastic Surgery 47: 297-300 (2020).
Kurup, et al., Suprachoroidal Drug Administration, Slide Deck, ASRS (2016).
Lee, et al., Effectiveness of Retrobulbar Hyaluronidase Injection in an Iatrogenic Blindness Rabbit Model Using Hyaluronic Acid Filler Injection, Plastic Reconstructive Surgery Journal 144: 137-143 (2019).
Shah, et al., Clinical Experience with the SCS Microinjector for Suprashoroidal Injections by Ophthalmologists, Slide Deck, American Society of Retina Specialists (Jul. 26-30, 2019).
Wasserman, Overview of recombinant human hyaluronidase-facilitated subcutaneous infusion of IgG in primary immunodeficiencies, Immunotherapy 6:553-567 (2014).
WIPO, PCT Form ISA237, Written Opinion for International Patent Application Serial No. PCT/US2021/025668, pp. 6 (dated Jul. 9, 2021).
WIPO, WIPO, PCT Form ISA210, International Search Report for International Patent Application Serial No. PCT/US2021/025668, pp. 3 (dated Jul. 9, 2021).

(Continued)

*Primary Examiner* — Nghi V Nguyen
(74) *Attorney, Agent, or Firm* — UltimatEdge IP Law Group, P.C.; Dean G. Stathakis

(57) ABSTRACT

The present disclosure discloses compositions comprising a hyaluronidase, devices comprising such compositions, as well as methods and uses employing such compositions and devices to reduce or eliminate a hyaluronic acid-induced blockage of one or more blood vessels supplying an eye of an individual; methods and uses for employing such compositions and devices to reduce or inhibit a vascular occlusion in an eye of an individual; and methods and uses for employing such compositions and devices to reduce or inhibit a hyaluronic acid-induced loss of vision of an individual.

20 Claims, 5 Drawing Sheets

(56) References Cited

OTHER PUBLICATIONS

Yoo, et al., Characterization of the Dynamics of Liquid and Gel Spread in the Suprachoroidal Space of Enucleated Porcine Eyes, Poster B0530, 2017 ARVO Annual Meeting (May 7-11, 2017).
Zhu, et al., Efficacy of Retrobulbar Hyaluronidase Injection for Vision Loss Resulting from Hyaluronic Acid Filler Embolization, Aesthetic Surgery Journal 38: 12-22 (2018).
Hartman, et al., Intravitreal, Subrentinal, and Suprashorodial Injections: Evolution and Microneedles for Drug Delivery, J. Ocul. Pharmacol. Therap. 34(1): 141-153 (2018).
USPTO, Non-Final Office Action for U.S. Appl. No. 17/394,804, pp. 15 (dated Feb. 15, 2022).
U.S. Appl. No. 17/394,804, filed Aug. 5, 2021, US 2021/0361752.
Halozyme, Hylenex Prescribing Information, pp. 9 (2016).
Morrow, et al. Comparative Pharmacokinetics and Insulin Action for Three Rapid-Acting Insulin Analogs Injected Subcutaneously With and Without Hyaluronidase, Diabetes Care 36: 273-275 (2013).
Muchmore, et al., Review of the Mechanism of Action and Clinical Efficacy of Recombinant Human Hyaluronidase Coadministration with Current Prandial Insulin Formulations, J. Diabetes Sci. Technol. 4(2): 419-428 2010).
Muchmore, et al., Accelerating and Improving the Consistency of Rapid-Acting Analog Insulin Absorption and Action for Both Subcutaneous Injection and Continuous Subcutaneous Infusion Using Recombinant Human Hyaluronidase, J. Diabetes Sci. Technol. 6(4): 764-772 (2012).
Thomas, et al., The INFUSE-Morphine Study: Use of Recombinant Human Hyaluronidase (rHuPH20) to Enhance the Absorption of Subcutaneously Administered Morphine in Patients with Advanced Illness, J. Pain Symptom Manage. 38 (5): 663-672 (2009).
Valeant, Vitrase Prescribing Information, pp. 2 (2017).
Vaughn, et al., Accelerated Pharmacokinetics and Glucodynamics of Prandial Insulins Injected with Recombinant Human Hyaluronidase, Diabetes Technol Ther. 11(6): 345-352 (2009); abstract only.
Adulkar, et al., An In Vitro Model Assessing the Penetration of Hyaluronidase through Optic Nerve Dura for Management of Hyaluronic Acid Facial Filler Embolism, Plast. Reconstr. Surg. 144: 43e-47e (2019).
Hwang, et al., Effectiveness of Retrobulbar Hyaluronidase Injection in an Iatrogenic Blindness Rabbit Model Using Hyaluronic Acid Filler Injection, Plast. Reconstr. Surg. 145: 658e (2020).
Navarro-Hernandez, et al., Effectiveness of Retrobulbar Hyaluronidase in the Treatment of Visual Loss Caused by Periocular Hyaluronic Acid Injection. A Systematic Review, Arch. Soc. Esp. Oftalmol. 97(9): 521-538 (2022).
Paap, et al., Examining the Role of Retrobulbar Hyaluronidase in Reversing Filler-Induced Blindness: A Systematic Review, Ophthalmic Plast. Reconstr. Surg. 36(3): 231-238 (2020).
Paap, et al., Assessing Retrobulbar Hyaluronidase as a Treatment for Filler-Induced Blindness in a Cadaver Model, Plast. Reconstr. Surg. 144(2): 315-320 (2019).
Silkiss, et al., Discussion: Assessing Retrobulbar Hyaluronidase as a Treatment for Filler-Induced Blindness in a Cadaver Model and Video Discussion: Treatment for Filler-Induced Blindness, Plast. Reconstr. Surg. 145(5): 999e-1001e (2020).
Zhu, et al., Efficacy of Retrobulbar Hyaluronidase Injection for Vision Loss Resulting from Hyaluronic Acid Filler Embolization, Aesthetic Surg. J. 38(1): 12-22 (2018).

\* cited by examiner

Central Retinal Artery Occlustion

Branch Retinal Artery Occlusion (Acute)

US 11,878,051 B2

REDUCING OR INHIBITING OCULAR DAMAGE BY HYALURONIDASE ADMINISTRATION

This application claims the benefit of priority and is entitled to the filing date pursuant to 35 U.S.C. § 119(e) of U.S. Provisional Patent Application 63/004,444, filed Apr. 2, 2020, the content of which is hereby incorporated by reference in its entirety.

FIELD OF THE INVENTION

The present invention relates to the treatment of loss of vision caused by administration of a hyaluronic acid soft-tissue dermal filler.

BACKGROUND

The use of fillers for augmentation of facial soft tissues in an individual has become one of the most commonly performed aesthetic procedures. For example, soft-tissue filler injection is the second most commonly performed cosmetic procedure following botulinum toxin treatment. The most commercially popular soft-tissue dermal fillers are ones employing hyaluronic acid.

Sadly, as the field of soft-tissue augmentation has become increasingly popular, reports of adverse events have increased. Loss of vision is one of the most tragic potential complications of a soft-tissue dermal filler injection. In particular, vascular occlusion from inadvertent intra-arterial injection of a soft-tissue dermal filler blocks blood flow to an eye, resulting in ischemia, necrosis, and loss of vision. To date, over 100 documented cases of vision loss after the administration of soft-tissue fillers have been reported. However, leading experts in soft-tissue augmentation suspect that this number of documented cases is a fraction of the actual number of occurrences of vision loss following the administration of soft-tissue fillers due to inconsistent reporting by providers of these services.

Unfortunately, there is no proven, effective treatment for loss of vision following a soft-tissue filler injection. Therefore, when an occlusive event occurs within these blood vessels, the loss of vision is permanent. Furthermore, even with early recognition of a vascular occlusion event, visual loss associated with soft-tissue filler injections is mostly irreversible unless blood flow can be quickly restored, which typically must take place within about 5 to about 15 minutes after the occlusion has occurred. Given the vulnerability of retinal tissue to a filler-induced vascular occlusion event, methods for reducing or eliminating this blockage are needed.

SUMMARY

The present disclosure provides such a solution for soft-tissue dermal fillers comprising hyaluronic acid. The compositions, devices, methods and uses disclosed herein administer a hyaluronidase to the suprachoroidal space of an eye. Such administration delivers a hyaluronidase into the blood vessels supplying an eye in about 5 minutes or less. This fast delivery of hyaluronidase enables this enzyme to reduce or eliminate the hyaluronic acid causing the vascular occlusion, thereby reducing or eliminating the risk of permanent damage to the eye.

Aspects of the present specification disclose methods of reducing or eliminating a hyaluronic acid-induced blockage in one or more blood vessels supplying blood to an eye in an individual in need thereof. The disclosed methods comprise administering a composition comprising a hyaluronidase to an individual in a manner that reduces or eliminates a hyaluronic acid-induced blockage in one or more blood vessels supplying blood to an eye. In aspects, the disclosed methods administer composition comprising a hyaluronidase to a suprachoroidal space of an eye. In other aspects, the disclosed methods administer a composition comprising a hyaluronidase using a delivery system, such as, e.g., a needle and syringe, an ADG needle, or a microinjector. The disclosed methods can administer a composition comprising a hyaluronidase in a single- or multi-dose amount ranging from about 15 IU to about 10,000 IU of a hyaluronidase.

Aspects of the present specification disclose methods of reducing or inhibiting a vascular occlusion in an eye of an individual in need thereof. The disclosed methods comprise administering a composition comprising a hyaluronidase to an individual in a manner that reduces or eliminates a hyaluronic acid-induced blockage in one or more blood vessels supplying blood to an eye, thereby reducing or inhibiting the vascular occlusion in the eye. In aspects, the disclosed methods administer composition comprising a hyaluronidase to a suprachoroidal space of an eye. In other aspects, the disclosed methods administer a composition comprising a hyaluronidase using a delivery system, such as, e.g., a needle and syringe, an ADG needle, or a microinjector. The disclosed methods can administer a composition comprising a hyaluronidase in a single- or multi-dose amount ranging from about 15 IU to about 10,000 IU of a hyaluronidase.

Aspects of the present specification disclose methods of reducing or inhibiting hyaluronic acid-induced loss of vision in an individual in need thereof. The disclosed methods comprise administering a composition comprising a hyaluronidase to an individual in a manner that reduces or eliminates a hyaluronic acid-induced blockage in one or more blood vessels supplying blood to an eye, thereby reducing or inhibiting the hyaluronic acid-induced loss of vision in the individual. In aspects, the disclosed methods administer a composition comprising a hyaluronidase to a suprachoroidal space of an eye. In other aspects, the disclosed methods administer a composition comprising a hyaluronidase using a delivery system, such as, e.g., a needle and syringe, an ADG needle, or a microinjector. The disclosed methods can administer a composition comprising a hyaluronidase in a single- or multi-dose amount ranging from about 15 IU to about 10,000 IU of a hyaluronidase.

Other aspects of the present specification disclose a delivery system, such as, e.g., a needle and syringe, an ADG needle, or a microinjector, comprising a composition comprising a hyaluronidase. In aspects, the disclosed delivery system delver a composition comprising a hyaluronidase to a suprachoroidal space of an eye. The disclosed delivery system can administer a composition comprising a hyaluronidase in a single or multi-dose amount ranging from about 15 IU to about 10,000 IU of a hyaluronidase.

Other aspects of the present specification disclose uses of a composition comprising a hyaluronidase. In aspects, the disclosed uses comprise a composition comprising a hyaluronidase contained in a delivery system, such as, e.g., a needle and syringe, ADG needle, or a microinjector. In other aspects, the disclosed uses comprise a composition comprising a hyaluronidase contained in a suprachoroidal microinjector. In other aspects, the disclosed uses comprise a composition comprising a hyaluronidase contained in an AGD needle. The disclosed uses can administer a composition comprising a hyaluronidase in a single- or multi-dose amount ranging from about 15 IU to about 10,000 IU of a hyaluronidase.

Other aspects of the present specification disclose uses of a delivery system, such as, e.g., a needle and syringe, ADG needle, or a microinjector, comprising a composition comprising a hyaluronidase. In aspects, the disclosed uses comprise a suprachoroidal microinjector comprising a composition comprising a hyaluronidase. In aspects, the disclosed uses comprise an ADG needle comprising a composition comprising a hyaluronidase. The disclosed uses can administer a composition comprising a hyaluronidase in a single- or multi-dose amount ranging from about 15 IU to about 10,000 IU of a hyaluronidase.

Other aspects of the present specification disclose uses of a composition comprising a hyaluronidase in the manufacture of a medicament. In aspects, the disclosed medicament comprises a composition comprising a hyaluronidase contained in a delivery system, such as, e.g., a needle and syringe, ADG needle, or a microinjector. In other aspects, the disclosed medicament comprises a composition comprising a hyaluronidase contained in a suprachoroidal microinjector. In other aspects, the disclosed medicament comprises a composition comprising a hyaluronidase contained in an ADG needle. The disclosed uses can administer a composition comprising a hyaluronidase in a single- or multi-dose amount ranging from about 50 IU to about 20,000 IU of a hyaluronidase.

Other aspects of the present specification disclose a composition comprising a hyaluronidase for use in inhibiting hyaluronic acid-induced blockage of one or more blood vessels supplying an eye. In aspects, a composition comprising a hyaluronidase is contained in a delivery system, such as, e.g., a needle and syringe, ADG needle, or a microinjector. In other aspects, a composition comprising a hyaluronidase is contained in a suprachoroidal microinjector. In other aspects, a composition comprising a hyaluronidase is contained in an ADG needle. The disclosed compositions comprising a hyaluronidase can contain a single- or multi-dose amount ranging from about 50 IU to about 20,000 IU of a hyaluronidase.

Other aspects of the present specification disclose a delivery system, such as, e.g., a needle and syringe, ADG needle, or a microinjector, comprising a composition comprising a hyaluronidase for use in inhibiting hyaluronic acid-induced blockage of one or more blood vessels supplying an eye. In aspects, a disclosed microinjector is a suprachoroidal microinjector. The disclosed delivery system comprising a composition comprising a hyaluronidase can contain a single- or multi-dose amount ranging from about 50 IU to about 20,000 IU of a hyaluronidase.

BRIEF DESCRIPTION OF THE DRAWINGS

The accompanying drawings, which are incorporated in and constitute a part of this specification, illustrate aspects of the disclosed subject matter in at least one of its exemplary embodiments, which are further defined in detail in the following description. Features, elements, and aspects of the disclosure are referenced by numerals with like numerals in different drawings representing the same, equivalent, or similar features, elements, or aspects, in accordance with one or more embodiments. The drawings are not necessarily to scale, emphasis instead being placed upon illustrating the principles herein described and provided by exemplary embodiments of the invention. In such drawings:

FIG. 6B showing cross-section of eye at injection site; FIG. 6C showing insertion of microinjector at the level of the suprachoroidal space; and FIG. 6D showing administration of a composition disclosed herein into the suprachoroidal space.

DETAILED DESCRIPTION

Figure 1:
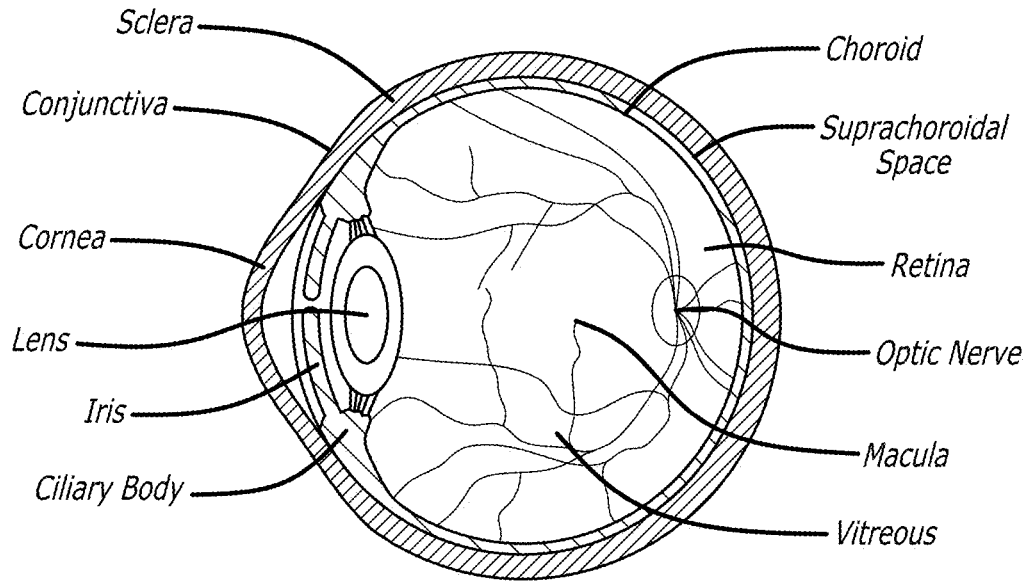
FIG. 1 is a cross-sectional view of a human eye showing its anatomical parts.

Eyes are organs of the visual system that detect light and convert it into electro-chemical impulses in neurons. In humans, the eyes are a complex optical system that collects light from the surrounding environment, regulates its intensity through a diaphragm, focuses it through an adjustable assembly of lenses to form an image, converts this image into a set of electrical signals, and transmits these signals to the brain through complex neural pathways that connect the eye via the optic nerve to the visual cortex and other areas of the brain. The major anatomical structures of a human eye are shown in FIG. 1.

Figure 2:
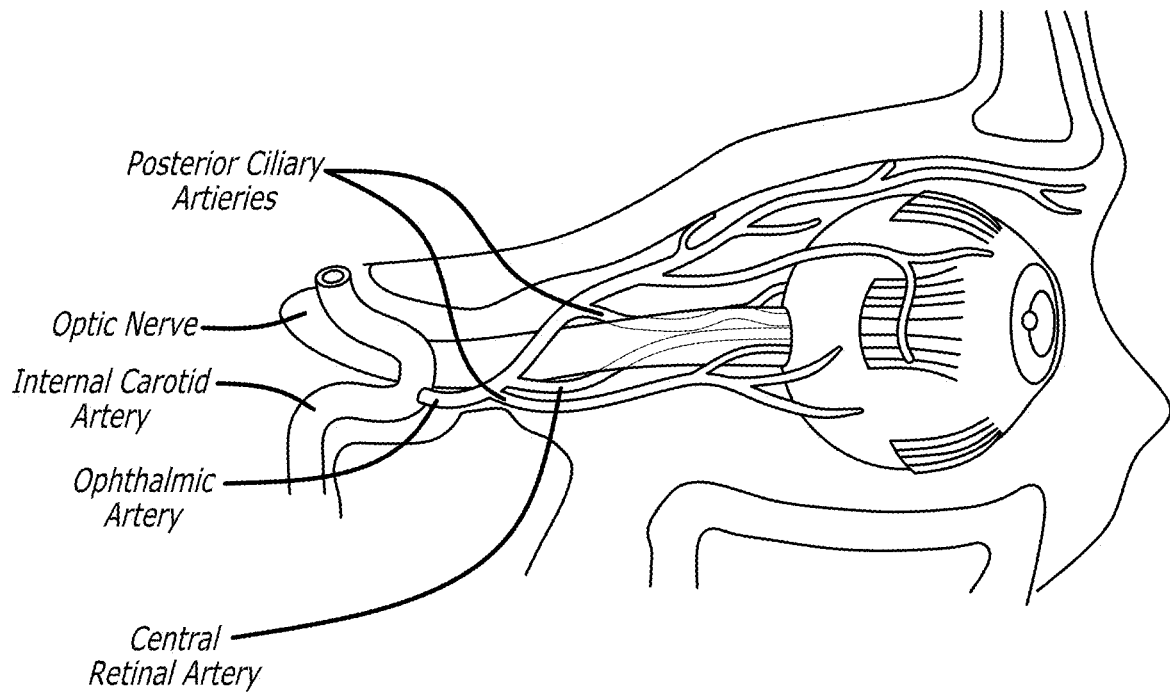
FIG. 2 illustrates the blood vessels associated with a human eye.

Blood vessels providing ophthalmic circulation to the eye are shown in FIG. 2. The central retinal artery, the short- and long-posterior ciliary arteries, the anterior ciliary arteries, and other arteries, all of which are branches from the ophthalmic artery, provide the arterial supply to the eye. The central retinal artery and the short-posterior ciliary arteries supply blood to the retina. The central retinal artery travels in or beside the optic nerve as the central retinal artery pierces the sclera and then branches to supply the layers of the inner retina with blood. Other branches of the ophthalmic artery provide nutrients to the eye and its muscles.

Figure 3:
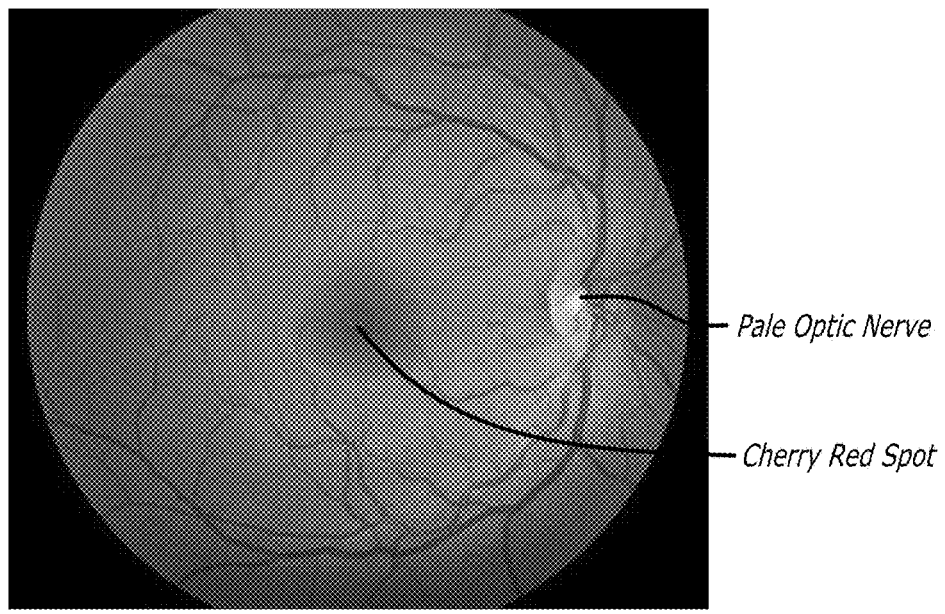
FIG. 3 is a photograph showing a central retinal artery occlusion.
Figure 4:
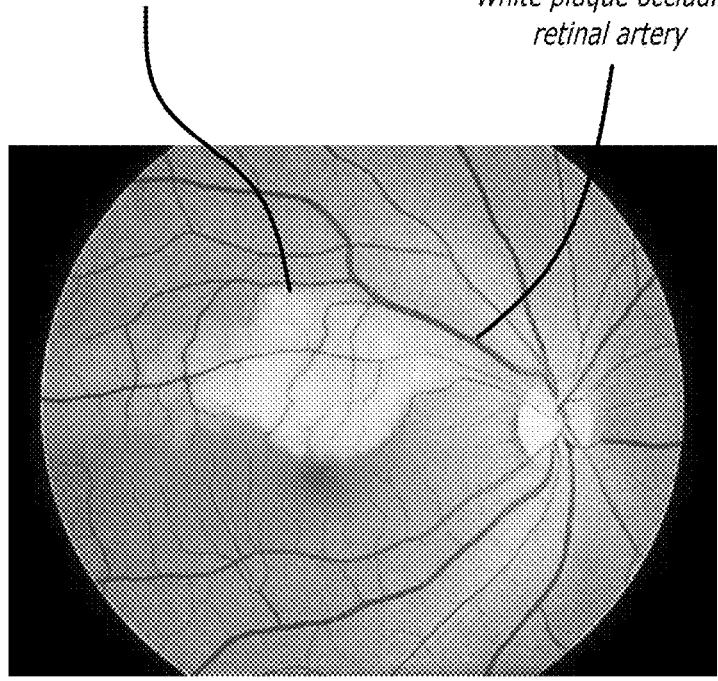
FIG. 4 is a photograph showing a branch retinal artery occlusion.

Unfortunately, administration of a soft-tissue dermal filler like a hyaluronic-acid filler to the face can result in filler entering the ophthalmic circulation, which leads to blockage of one or more vessels supplying an eye. Such blockage impedes or prevents blood flow, resulting in the deprivation of oxygen and nutrients to the eye from the occluded vessel (FIGS. 3 & 4). If blood flow through the occluded vessel is not restored quickly, ocular ischemia and/or retinal damage with corresponding necrosis and loss of vision may result. These adverse events happen rapidly, with permanent injury occurring in as little as minutes after such ophthalmic vascular occlusion.

Hyaluronidases are a family of enzymes that catalyze the degradation of hyaluronic acid. Thus, one possible solution to a hyaluronic acid-induced blockage of one or more vessels supplying an eye is to administer a hyaluronidase to this site of blockage. However, there is currently no known way to effectively deliver hyaluronidase to the ophthalmic circulation in a manner that would reduce or eliminate hyaluronic acid-induced blockage of the ophthalmic circulation.

The compositions, devices, methods and uses disclosed herein effectively deliver hyaluronidase to the ophthalmic circulation in a manner that would reduce or eliminate hyaluronic acid-induced blockage to one or more blood vessels supplying an eye. Such reduction or elimination of hyaluronic acid-induced vascular occlusion involves the administration of a hyaluronidase to a suprachoroidal space of an eye. Such administration ultimately delivers a hyaluronidase into the blood vessels supplying an eye in about 90 minutes or less, preferably 60 minutes or less, more preferably 30 minutes or less, and most preferably 5 to 15 minutes or less. This fast delivery of hyaluronidase enables this enzyme to reduce or eliminate the hyaluronic acid causing the vascular occlusion, thereby reducing or eliminating the risk of permanent damage to the eye.

Aspects of the present specification disclose a pharmaceutical composition. A pharmaceutical composition disclosed herein refers to a therapeutically effective concentration of an active ingredient, such as, e.g., a hyaluronidase disclosed herein. Preferably, the pharmaceutical composition disclosed herein does not produce an adverse, allergic, or other untoward or unwanted reaction when administered to an individual. A pharmaceutical composition disclosed herein is useful for medical and veterinary applications. A pharmaceutical composition disclosed herein may be formulated as a liquid pharmaceutical composition or as a dried pharmaceutical composition, such as, e.g., a lyophilized or freeze-dried formulation. A pharmaceutical composition disclosed herein may be administered alone to an individual or in combination with supplementary active compounds, agents, drugs or hormones.

Aspects of the present specification disclose a hyaluronidase. Hyaluronidase hydrolyses hyaluronic acid. According to their enzymatic mechanism, hyaluronidases are hyaluronoglucosidases (EC 3.2.1.35), i.e., they cleave the (1→4)-linkages between N-acetylglucosamine and glucuronate. The term "hyaluronidase" may also refer to hyaluronoglucuronidases (EC 3.2.1.36), which cleave (1→3)-linkages. Pharmacokinetics of hyaluronidase have been assessed in animal studies after intravitreous injection. The plasma half-life is 49 hours. The highest concentrations are achieved in vitreous, retina, and sclera. The half-life in oculartissues is between 60 and 112 hours. Hyaluronidase can be commercially obtained from animals, where it is typically extracted from ovine or bovine testicles (Vitrase, Bausch Health Companies, Inc., Laval, Quebec, Canada), leech, or bacteria. Hyaluronidase can also be obtained recombinantly, e.g., by genetically manipulating human recombinant DNA in Chinese hamster ovary cells (Hylenex, Halozyme Therapeutics, Inc., San Diego, Calif.).

The present specification discloses, in part, a therapeutically effective amount. A therapeutically effective amount of a hyaluronidase is an amount sufficient to reduce or eliminate a hyaluronic acid-induced blockage in one or more blood vessels of an eye. In aspects of this embodiment, a therapeutically effective amount of a hyaluronidase is an amount sufficient to reduce one or more physiological conditions or symptoms associated with a hyaluronic acid-induced blockage in one or more blood vessels of an eye or an amount sufficient to protect the individual against one or more physiological conditions or symptoms associated with a hyaluronic acid-induced blockage in one or more blood vessels of an eye. As used herein, the term "therapeutically effective amount" includes the terms "amount sufficient", "therapeutically sufficient amount", "effective amount", "effective dose", or "therapeutically effective dose" and refers to the minimum amount of a hyaluronidase necessary to achieve the desired therapeutic effect and includes an amount sufficient to reduce or inhibit one or more physiological conditions or symptoms associated with a hyaluronic acid-induced blockage in one or more blood vessels of an eye.

In aspects of this embodiment, a therapeutically effective amount of a hyaluronidase disclosed herein reduces or inhibits one or more physiological conditions or symptoms associated with a hyaluronic acid-induced blockage in one or more blood vessels of an eye by, e.g., at least 10%, at least 20%, at least 30%, at least 40%, at least 50%, at least 60%, at least 70%, at least 80%, at least 90% or at least 100%. In other aspects of this embodiment, an effective amount of a hyaluronidase disclosed herein reduces or inhibits one or more physiological conditions or symptoms associated with a hyaluronic acid-induced blockage in one or more blood vessels of an eye by, e.g., at most 10%, at most 20%, at most 30%, at most 40%, at most 50%, at most 60%, at most 70%, at most 80%, at most 90% or at most 100%. In yet other aspects of this embodiment, an effective amount of a hyaluronidase disclosed herein reduces or inhibits one or more physiological conditions or symptoms associated with a hyaluronic acid-induced blockage in one or more blood vessels of an eye by, e.g., about 10% to about 100%, about 10% to about 90%, about 10% to about 80%, about 10% to about 70%, about 10% to about 60%, about 10% to about 50%, about 10% to about 40%, about 10% to about 30%, about 10% to about 20%, about 20% to about 100%, about 20% to about 90%, about 20% to about 80%, about 20% to about 70%, about 20% to about 60%, about 20% to about 50%, about 20% to about 40%, about 20% to about 30%, about 30% to about 100%, about 30% to about 90%, about 30% to about 80%, about 30% to about 70%, about 30% to about 60%, about 30% to about 50%, about 30% to about 40%, about 40% to about 100%, about 40% to about 90%, about 40% to about 80%, about 40% to about 70%, about 40% to about 60%, about 40% to about 50%, about 50% to about 100%, about 50% to about 90%, about 50% to about 80%, about 50% to about 70%, about 50% to about 60%, about 60% to about 100%, about 60% to about 90%, about 60% to about 80%, about 60% to about 70%, about 70% to about 100%, about 70% to about 90%, about 70% to about 80%, about 80% to about 100%, about 80% to about 90%, or about 90% to about 100%. In still other aspects of this embodiment, an effective amount of a hyaluronidase disclosed herein reduces or inhibits one or more physiological conditions or symptoms associated with a hyaluronic acid-induced blockage in one or more blood vessels of an eye for, e.g., at least one week, at least one month, at least two months, at least three months, at least four months, at least five months, at least six months, at least seven months, at least eight months, at least nine months, at least ten months, at least eleven months, or at least twelve months.

In aspects of this embodiment, a therapeutically effective amount of a hyaluronidase disclosed herein restores or maintains one or more qualitative or quantitative aspects of vision by, e.g., at least 10%, at least 20%, at least 30%, at least 40%, at least 50%, at least 60%, at least 70%, at least 80%, at least 90% or at least 100%. In other aspects of this embodiment, an effective amount of a hyaluronidase disclosed herein restores or maintains one or more qualitative or quantitative aspects of vision by, e.g., at most 10%, at most 20%, at most 30%, at most 40%, at most 50%, at most 60%, at most 70%, at most 80%, at most 90% or at most 100%. In yet other aspects of this embodiment, an effective amount of a hyaluronidase disclosed herein restores or maintains one or more qualitative or quantitative aspects of vision by, e.g., about 10% to about 100%, about 10% to about 90%, about 10% to about 80%, about 10% to about 70%, about 10% to about 60%, about 10% to about 50%, about 10% to about 40%, about 10% to about 30%, about 10% to about 20%, about 20% to about 100%, about 20% to about 90%, about 20% to about 80%, about 20% to about 70%, about 20% to about 60%, about 20% to about 50%, about 20% to about 40%, about 20% to about 30%, about 30% to about 100%, about 30% to about 90%, about 30% to about 80%, about 30% to about 70%, about 30% to about 60%, about 30% to about 50%, about 30% to about 40%, about 40% to about 100%, about 40% to about 90%, about 40% to about 80%, about 40% to about 70%, about 40% to about 60%, about 40% to about 50%, about 50% to about 100%, about 50% to about 90%, about 50% to about 80%, about 50% to about 70%, about 50% to about 60%, about 60% to about 100%, about 60% to about 90%, about 60% to about 80%, about 60% to about 70%, about 70% to about 100%, about 70% to about 90%, about 70% to about 80%, about 80% to about 100%, about 80% to about 90%, or about 90% to about 100%. In still other aspects of this embodiment, an effective amount of a hyaluronidase disclosed herein restores or maintains one or more qualitative or quantitative aspects of vision for, e.g., at least one week, at least one month, at least two months, at least three months, at least four months, at least five months, at least six months, at least seven months, at least eight months, at least nine months, at least ten months, at least eleven months, or at least twelve months.

The actual therapeutic effective amount of a hyaluronidase disclosed herein to be used or administered to an individual can be determined by a person of ordinary skill in the art by taking into account factors that include, without limitation, the type of hyaluronic acid-induced blockage, the particular physiological conditions or symptoms associated with a hyaluronic acid-induced blockage, the cause of a hyaluronic acid-induced blockage, the severity of a hyaluronic acid-induced blockage, the degree of relief desired for a hyaluronic acid-induced blockage, the duration of relief desired for a hyaluronic acid-induced blockage, the particular soft-tissue dermal filler used, the rate of excretion of the particular hyaluronidase used, the pharmacodynamics of the particular hyaluronidase used, the nature of the other compounds to be included in the therapy, the particular route of administration used, the particular characteristics, history and risk factors of the individual, such as, e.g., age, weight, general health and the like, or any combination thereof. It is known by a person of ordinary skill in the art that an effective amount of a hyaluronidase disclosed herein can be extrapolated from in-vitro assays and in-vivo administration studies using animal models prior to administration to humans. Variations in dosage levels can be adjusted using standard empirical routines of optimization, which are well-known to a person of ordinary skill in the art. The precise therapeutically effective dosage levels and patterns are preferably determined by the attending healthcare professional in consideration of the above-identified factors.

Depending on the concentration of hyaluronidase in a composition disclosed herein, dosing can be a single-dose administration or multiple-dose administration. Typically, when formulated as a single dose, the concentration of hyaluronidase in a composition disclosed herein is one that effectively reduces or eliminates a hyaluronic acid-induced blockage in one or more blood vessels of an eye. When a composition disclosed herein is formulated for multi-dose administration, the total amount of hyaluronidase cumulatively administered by the multiple doses is one that effectively reduces or eliminates a hyaluronic acid-induced blockage in one or more blood vessels of an eye.

A composition disclosed herein can comprising a hyaluronidase in a concentration between about 15 IU/mL and about 20,000 IU/mL. In aspects of this embodiment, a composition disclosed herein comprises a hyaluronidase in a concentration of, e.g., at least 15 IU/mL, at least 25 IU/mL, at least 50 IU/mL, at least 100 IU/mL, at least 200 IU/mL, at least 300 IU/mL, at least 450 IU/mL, at least 600 IU/mL, at least 900 IU/mL, at least 1,000 IU/mL, at least 1,250 IU/mL, at least 1,500 IU/mL, at least 1,750 IU/mL, at least 2,000 IU/mL, at least 3,000 IU/mL, at least 4,000 IU/mL, at least 5,000 IU/mL, at least 6,000 IU/mL, at least 7,000 IU/mL, at least 8,000 IU/mL, at least 9,000 IU/mL, at least 10,000 IU/mL, at least 11,000 IU/mL, at least 12,000 IU/mL, at least 13,000 IU/mL, at least 14,000 IU/mL, at least 15,000 IU/mL, at least 16,000 IU/mL, at least 17,000 IU/mL, at least 18,000 IU/mL, at least 19,000 IU/mL, or at least 20,000 IU/mL.

In other aspects of this embodiment, a composition disclosed herein comprises a hyaluronidase in a concentration of, e.g., at most 15 IU/mL, at most 25 IU/mL, at most 50 IU/mL, at most 100 IU/mL, at most 200 IU/mL, at most 300 IU/mL, at most 450 IU/mL, at most 600 IU/mL, at most 900 IU/mL, at most 1,000 IU/mL, at most 1,250 IU/mL, at most 1,500 IU/mL, at most 1,750 IU/mL, at most 2,000 IU/mL, at most 3,000 IU/mL, at most 4,000 IU/mL, at most 5,000 IU/mL, at most 6,000 IU/mL, at most 7,000 IU/mL, at most 8,000 IU/mL, at most 9,000 IU/mL, at most 10,000 IU/mL, at most 11,000 IU/mL, at most 12,000 IU/mL, at most 13,000 IU/mL, at most 14,000 IU/mL, at most 15,000 IU/mL, at most 16,000 IU/mL, at most 17,000 IU/mL, at most 18,000 IU/mL, at most 19,000 IU/mL, or at most 20,000 IU/mL.

In yet other aspects of this embodiment, a composition disclosed herein comprises a hyaluronidase in a concentration of, e.g., about 15 IU/mL to about 25 IU/mL, about 15 IU/mL to about 50 IU/mL, about 15 IU/mL to about 100 IU/mL, about 15 IU/mL to about 200 IU/mL, about 15 IU/mL to about 300 IU/mL, about 15 IU/mL to about 400 IU/mL, about 15 IU/mL to about 450 IU/mL, about 15 IU/mL to about 600 IU/mL, about 15 IU/mL to about 750 IU/mL, about 15 IU/mL to about 900 IU/mL, about 25 IU/mL to about 50 IU/mL, about 25 IU/mL to about 100 IU/mL, about 25 IU/mL to about 200 IU/mL, about 25 IU/mL to about 300 IU/mL, about 25 IU/mL to about 400 IU/mL, about 25 IU/mL to about 450 IU/mL, about 25 IU/mL to about 600 IU/mL, about 25 IU/mL to about 750 IU/mL, about 25 IU/mL to about 900 IU/mL, about 50 IU/mL to about 100 IU/mL, about 50 IU/mL to about 200 IU/mL, about 50 IU/mL to about 300 IU/mL, about 50 IU/mL to about 400 IU/mL, about 50 IU/mL to about 450 IU/mL, about 50 IU/mL to about 600 IU/mL, about 50 IU/mL to about 750 IU/mL, about 50 IU/mL to about 900 IU/mL, about 100 IU/mL to about 200 IU/mL, about 100 IU/mL to about 300 IU/mL, about 100 IU/mL to about 400 IU/mL, about 100 IU/mL to about 450 IU/mL, about 100 IU/mL to about 600 IU/mL, about 100 IU/mL to about 750 IU/mL, about 100 IU/mL to about 900 IU/mL, about 200 IU/mL to about 300 IU/mL, about 200 IU/mL to about 400 IU/mL, about 200 IU/mL to about 450 IU/mL, about 200 IU/mL to about 600 IU/mL, about 200 IU/mL to about 750 IU/mL, about 200 IU/mL to about 900 IU/mL, about 300 IU/mL to about 450 IU/mL, about 300 IU/mL to about 600 IU/mL, about 300 IU/mL to about 750 IU/mL, about 300 IU/mL to about 900 IU/mL, about 450 IU/mL to about 600 IU/mL, about 450 IU/mL to about 750 IU/mL, about 450 IU/mL to about 900 IU/mL, about 450 IU/mL to about 1,000 IU/mL, about 450 IU/mL to about 1,250 IU/mL, about 600

IU/mL to about 750 IU/mL, about 600 IU/mL to about 900 IU/mL, about 600 IU/mL to about 1,000 IU/mL, about 600 IU/mL to about 1,250 IU/mL, about 600 IU/mL to about 1,500 IU/mL, about 750 IU/mL to about 900 IU/mL, about 750 IU/mL to about 1,000 IU/mL, about 750 IU/mL to about 1,250 IU/mL, about 750 IU/mL to about 1,500 IU/mL, about 750 IU/mL to about 1,750 IU/mL, about 900 IU/mL to about 1,000 IU/mL, about 900 IU/mL to about 1,250 IU/mL, about 900 IU/mL to about 1,500 IU/mL, about 900 IU/mL to about 1,750 IU/mL, about 900 IU/mL to about 2,000 IU/mL, about 1,000 IU/mL to about 1,250 IU/mL, about 1,000 IU/mL to about 1,500 IU/mL, about 1,000 IU/mL to about 1,750 IU/mL, about 1,000 IU/mL to about 2,000 IU/mL, about 1,000 IU/mL to about 3,000 IU/mL, about 1,000 IU/mL to about 4,000 IU/mL, about 1,000 IU/mL to about 5,000 IU/mL, about 1,000 IU/mL to about 6,000 IU/mL, about 1,000 IU/mL to about 7,000 IU/mL, about 1,000 IU/mL to about 8,000 IU/mL, about 1,000 IU/mL to about 9,000 IU/mL, about 1,000 IU/mL to about 10,000 IU/mL, about 2,000 IU/mL to about 3,000 IU/mL, about 2,000 IU/mL to about 4,000 IU/mL, about 2,000 IU/mL to about 5,000 IU/mL, about 2,000 IU/mL to about 6,000 IU/mL, about 2,000 IU/mL to about 7,000 IU/mL, about 2,000 IU/mL to about 8,000 IU/mL, about 2,000 IU/mL to about 9,000 IU/mL, about 2,000 IU/mL to about 10,000 IU/mL, about 2,500 IU/mL to about 3,000 IU/mL, about 2,500 IU/mL to about 4,000 IU/mL, about 2,500 IU/mL to about 5,000 IU/mL, about 2,500 IU/mL to about 6,000 IU/mL, about 2,500 IU/mL to about 7,000 IU/mL, about 2,500 IU/mL to about 8,000 IU/mL, about 2,500 IU/mL to about 9,000 IU/mL, about 2,500 IU/mL to about 10,000 IU/mL, about 3,000 IU/mL to about 4,000 IU/mL, about 3,000 IU/mL to about 5,000 IU/mL, about 3,000 IU/mL to about 6,000 IU/mL, about 3,000 IU/mL to about 7,000 IU/mL, about 3,000 IU/mL to about 8,000 IU/mL, about 3,000 IU/mL to about 9,000 IU/mL, about 3,000 IU/mL to about 10,000 IU/mL, about 4,000 IU/mL to about 5,000 IU/mL, about 4,000 IU/mL to about 6,000 IU/mL, about 4,000 IU/mL to about 7,000 IU/mL, about 4,000 IU/mL to about 8,000 IU/mL, about 4,000 IU/mL to about 9,000 IU/mL, about 4,000 IU/mL to about 10,000 IU/mL, about 5,000 IU/mL to about 6,000 IU/mL, about 5,000 IU/mL to about 7,000 IU/mL, about 5,000 IU/mL to about 8,000 IU/mL, about 5,000 IU/mL to about 9,000 IU/mL, about 5,000 IU/mL to about 10,000 IU/mL, about 6,000 IU/mL to about 7,000 IU/mL, about 6,000 IU/mL to about 8,000 IU/mL, about 6,000 IU/mL to about 9,000 IU/mL, about 6,000 IU/mL to about 10,000 IU/mL, about 7,000 IU/mL to about 8,000 IU/mL, about 7,000 IU/mL to about 9,000 IU/mL, about 7,000 IU/mL to about 10,000 IU/mL, about 8,000 IU/mL to about 9,000 IU/mL, about 8,000 IU/mL to about 10,000 IU/mL, or about 9,000 IU/mL to about 10,000 IU/mL.

In yet other aspects of this embodiment, a composition disclosed herein comprises a hyaluronidase in a concentration of, e.g., about 10,000 IU/mL to about 11,000 IU/mL, about 10,000 IU/mL to about 12,000 IU/mL, about 10,000 IU/mL to about 13,000 IU/mL, about 10,000 IU/mL to about 14,000 IU/mL, about 10,000 IU/mL to about 15,000 IU/mL, about 10,000 IU/mL to about 16,000 IU/mL, about 10,000 IU/mL to about 17,000 IU/mL, about 10,000 IU/mL to about 18,000 IU/mL, about 10,000 IU/mL to about 19,000 IU/mL, about 10,000 IU/mL to about 20,000 IU/mL, about 11,000 IU/mL to about 12,000 IU/mL, about 11,000 IU/mL to about 13,000 IU/mL, about 11,000 IU/mL to about 14,000 IU/mL, about 11,000 IU/mL to about 15,000 IU/mL, about 11,000 IU/mL to about 16,000 IU/mL, about 11,000 IU/mL to about 17,000 IU/mL, about 11,000 IU/mL to about 18,000 IU/mL, about 11,000 IU/mL to about 19,000 IU/mL, about 11,000 IU/mL to about 20,000 IU/mL, about 12,000 IU/mL to about 13,000 IU/mL, about 12,000 IU/mL to about 14,000 IU/mL, about 12,000 IU/mL to about 15,000 IU/mL, about 12,000 IU/mL to about 16,000 IU/mL, about 12,000 IU/mL to about 17,000 IU/mL, about 12,000 IU/mL to about 18,000 IU/mL, about 12,000 IU/mL to about 19,000 IU/mL, about 12,000 IU/mL to about 20,000 IU/mL, about 13,000 IU/mL to about 14,000 IU/mL, about 13,000 IU/mL to about 15,000 IU/mL, about 13,000 IU/mL to about 16,000 IU/mL, about 13,000 IU/mL to about 17,000 IU/mL, about 13,000 IU/mL to about 18,000 IU/mL, about 13,000 IU/mL to about 19,000 IU/mL, about 13,000 IU/mL to about 20,000 IU/mL, about 14,000 IU/mL to about 15,000 IU/mL, about 14,000 IU/mL to about 16,000 IU/mL, about 14,000 IU/mL to about 17,000 IU/mL, about 14,000 IU/mL to about 18,000 IU/mL, about 14,000 IU/mL to about 19,000 IU/mL, about 14,000 IU/mL to about 20,000 IU/mL, about 15,000 IU/mL to about 16,000 IU/mL, about 15,000 IU/mL to about 17,000 IU/mL, about 15,000 IU/mL to about 18,000 IU/mL, about 15,000 IU/mL to about 19,000 IU/mL, about 15,000 IU/mL to about 20,000 IU/mL, about 16,000 IU/mL to about 17,000 IU/mL, about 16,000 IU/mL to about 18,000 IU/mL, about 16,000 IU/mL to about 19,000 IU/mL, about 16,000 IU/mL to about 20,000 IU/mL, about 17,000 IU/mL to about 18,000 IU/mL, about 17,000 IU/mL to about 19,000 IU/mL, about 17,000 IU/mL to about 20,000 IU/mL, about 18,000 IU/mL to about 19,000 IU/mL, about 18,000 IU/mL to about 20,000 IU/mL, or about 19,000 IU/mL to about 20,000 IU/mL.

A single-dose amount of a composition comprising a hyaluronidase used to effectively reduce or eliminate a hyaluronic acid-induced blockage in one or more blood vessels of an eye can include between about 15 IU and about 10,000 IU of a hyaluronidase. In aspects of this embodiment, a single-dose amount of a composition comprising a hyaluronidase used to effectively reduce or eliminate a hyaluronic acid-induced blockage in one or more blood vessels of an eye can include a hyaluronidase in an amount of, e.g., at least 15 IU, at least 25 IU, at least 50 IU, at least 100 IU, at least 200 IU, at least 300 IU, at least 450 IU, at least 600 IU, at least 900 IU, at least 1,000 IU, at least 1,250 IU, at least 1,500 IU, at least 1,750 IU, at least 2,000 IU, at least 3,000 IU, at least 4,000 IU, at least 5,000 IU, at least 6,000 IU, at least 7,000 IU, at least 8,000 IU, at least 9,000 IU, or at least 10,000 IU. In other aspects of this embodiment, a single-dose amount of a composition comprising a hyaluronidase used to effectively reduce or eliminate a hyaluronic acid-induced blockage in one or more blood vessels of an eye can include a hyaluronidase in an amount of, e.g., at most 15 IU, at most 25 IU, at most 50 IU, at most 100 IU, at most 200 IU, at most 300 IU, at most 450 IU, at most 600 IU, at most 900 IU, at most 1,000 IU, at most 1,250 IU, at most 1,500 IU, at most 1,750 IU, at most 2,000 IU, at most 3,000 IU, at most 4,000 IU, at most 5,000 IU, at most 6,000 IU, at most 7,000 IU, at most 8,000 IU, at most 9,000 IU, or at most 10,000 IU.

In yet other aspects of this embodiment, a single-dose amount of a composition comprising a hyaluronidase used to effectively reduce or eliminate a hyaluronic acid-induced blockage in one or more blood vessels of an eye can include a hyaluronidase in an amount of, e.g., about 15 IU to about 25 IU, about 15 IU to about 50 IU, about 15 IU to about 100 IU, about 15 IU to about 200 IU, about 15 IU to about 300 IU, about 15 IU to about 400 IU, about 15 IU to about 450 IU, about 15 IU to about 600 IU, about 15 IU to about 750 IU, about 15 IU to about 900 IU, about 25 IU to about 50 IU, about 25 IU to about 100 IU, about 25 IU to about 200 IU, about 25 IU to about 300 IU, about 25 IU to about 400 IU, about 25 IU to about 450 IU, about 25 IU to about 600 IU, about 25 IU to about 750 IU, about 25 IU to about 900 IU, about 50 IU to about 100 IU, about 50 IU to about 200 IU, about 50 IU to about 300 IU, about 50 IU to about 400 IU, about 50 IU to about 450 IU, about 50 IU to about 600 IU, about 50 IU to about 750 IU, about 50 IU to about 900 IU, about 100 IU to about 200 IU, about 100 IU to about 300 IU, about 100 IU to about 400 IU, about 100 IU to about 450 IU, about 100 IU to about 600 IU, about 100 IU to about 750 IU, about 100 IU to about 900 IU, about 200 IU to about 300 IU, about 200 IU to about 400 IU, about 200 IU to about 450 IU, about 200 IU to about 600 IU, about 200 IU to about 750 IU, about 200 IU to about 900 IU, about 300 IU to about 450 IU, about 300 IU to about 600 IU, about 300 IU to about 750 IU, about 300 IU to about 900 IU, about 450 IU to about 600 IU, about 450 IU to about 750 IU, about 450 IU to about 900 IU, about 450 IU to about 1,000 IU, about 450 IU to about 1,250 IU, about 600 IU to about 750 IU, about 600 IU to about 900 IU, about 600 IU to about 1,000 IU, about 600 IU to about 1,250 IU, about 600 IU to about 1,500 IU, about 750 IU to about 900 IU, about 750 IU to about 1,000 IU, about 750 IU to about 1,250 IU, about 750 IU to about 1,500 IU, about 750 IU to about 1,750 IU, about 900 IU to about 1,000 IU, about 900 IU to about 1,250 IU, about 900 IU to about 1,500 IU, about 900 IU to about 1,750 IU, about 900 IU to about 2,000 IU, about 1,000 IU to about 1,250 IU, about 1,000 IU to about 1,500 IU, about 1,000 IU to about 1,750 IU, about 1,000 IU to about 2,000 IU, about 1,000 IU to about 3,000 IU, about 1,000 IU to about 4,000 IU, about 1,000 IU to about 5,000 IU, about 1,000 IU to about 6,000 IU, about 1,000 IU to about 7,000 IU, about 1,000 IU to about 8,000 IU, about 1,000 IU to about 9,000 IU, about 1,000 IU to about 10,000 IU, about 2,000 IU to about 3,000 IU, about 2,000 IU to about 4,000 IU, about 2,000 IU to about 5,000 IU, about 2,000 IU to about 6,000 IU, about 2,000 IU to about 7,000 IU, about 2,000 IU to about 8,000 IU, about 2,000 IU to about 9,000 IU, about 2,000 IU to about 10,000 IU, about 2,500 IU to about 3,000 IU, about 2,500 IU to about 4,000 IU, about 2,500 IU to about 5,000 IU, about 2,500 IU to about 6,000 IU, about 2,500 IU to about 7,000 IU, about 2,500 IU to about 8,000 IU, about 2,500 IU to about 9,000 IU, about 2,500 IU to about 10,000 IU, about 3,000 IU to about 4,000 IU, about 3,000 IU to about 5,000 IU, about 3,000 IU to about 6,000 IU, about 3,000 IU to about 7,000 IU, about 3,000 IU to about 8,000 IU, about 3,000 IU to about 9,000 IU, about 3,000 IU to about 10,000 IU, about 4,000 IU to about 5,000 IU, about 4,000 IU to about 6,000 IU, about 4,000 IU to about 7,000 IU, about 4,000 IU to about 8,000 IU, about 4,000 IU to about 9,000 IU, about 4,000 IU to about 10,000 IU, about 5,000 IU to about 6,000 IU, about 5,000 IU to about 7,000 IU, about 5,000 IU to about 8,000 IU, about 5,000 IU to about 9,000 IU, about 5,000 IU to about 10,000 IU, about 6,000 IU to about 7,000 IU, about 6,000 IU to about 8,000 IU, about 6,000 IU to about 9,000 IU, about 6,000 IU to about 10,000 IU, about 7,000 IU to about 8,000 IU, about 7,000 IU to about 9,000 IU, about 7,000 IU to about 10,000 IU, about 8,000 IU to about 9,000 IU, about 8,000 IU to about 10,000 IU, or about 9,000 IU to about 10,000 IU.

With respect to a multi-dose administration of a composition comprising a hyaluronidase disclosed herein, the administration of all doses should occur quickly in order to be as effective as possible in reducing or eliminating a hyaluronic acid-induced blockage in one or more blood vessels of an eye. In aspects of this embodiment, all doses of a multi-dose administration occur within, e.g., at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 30 minutes, at least 45 minutes, at least 60 minutes, at least 75 minutes or at least 90 minutes. In other aspects of this embodiment, all doses of a multi-dose administration occur within, e.g., at most 2 minutes, at most 3 minutes, at most 4 minutes, at most 5 minutes, at most 6 minutes, at most 7 minutes, at most 8 minutes, at most 9 minutes, at most 10 minutes, at most 11 minutes, at most 12 minutes, at most 13 minutes, at most 14 minutes, at most 15 minutes, at most 30 minutes, at most 45 minutes, at most 60 minutes, at most 75 minutes or at most 90 minutes. In yet other aspects of this embodiment, all doses of a multi-dose administration occur within, e.g., about 2 to about 3 minutes, about 2 to about 4 minutes, about 2 to about 5 minutes, about 2 to about 6 minutes, about 3 to about 4 minutes, about 3 to about 5 minutes, about 3 to about 6 minutes, about 4 to about 5 minutes, about 4 to about 6 minutes, about 5 to about 6 minutes, about 5 to about 7 minutes, about 5 to about 8 minutes, about 5 to about 9 minutes, about 5 to about 10 minutes, about 5 to about 11 minutes, about 6 to about 7 minutes, about 6 to about 8 minutes, about 6 to about 9 minutes, about 6 to about 10 minutes, about 6 to about 11 minutes, about 7 to about 8 minutes, about 7 to about 9 minutes, about 7 to about 10 minutes, about 7 to about 11 minutes, about 8 to about 9 minutes, about 8 to about 10 minutes, about 8 to about 11 minutes, about 9 to about 10 minutes, about 9 to about 11 minutes, about 10 to about 11 minutes, about 10 to about 12 minutes, about 10 to about 13 minutes, about 10 to about 14 minutes, about 10 to about 15 minutes, about 11 to about 12 minutes, about 11 to about 13 minutes, about 11 to about 14 minutes, about 11 to about 15 minutes, about 12 to about 13 minutes, about 12 to about 14 minutes, about 12 to about 15 minutes, about 13 to about 14 minutes, about 13 to about 15 minutes, or about 14 to about 15 minutes. In still other aspects of this embodiment, the number of doses administered in a multi-dose administration is from, e.g., about 2 to about 5 minutes, about 2 to about 10 minutes, about 2 to about 15 minutes, about 5 to about 10 minutes, about 5 to about 15 minutes, about 5 minutes to about 30 minutes, about 10 minutes to about 15 minutes, about 10 minutes to about 30 minutes, about 15 minutes to about 30 minutes, about 15 minutes to about 45 minutes, about 15 minutes to about 60 minutes, about 15 minutes to about 75 minutes, or about 15 minutes to about 90 minutes.

With respect to a multi-dose administration of a composition comprising a hyaluronidase disclosed herein, the number of doses administered is the number needed to achieve an effective amount of hyaluronidase in order to reduce or eliminate a hyaluronic acid-induced blockage in one or more blood vessels of an eye. In aspects of this embodiment, the number of doses administered in a multi-dose administration is, e.g., at least 2, at least 3, at least 4, at least 5, at least 6, at least 7, at least 8, at least 9, at least 10, at least 11, at least 12, at least 13, at least 14, or at least 15. In other aspects of this embodiment, the number of doses administered in a multi-dose administration is, e.g., at most 2, at most 3, at most 4, at most 5, at most 6, at most 7, at most 8, at most 9, at most 10, at most 11, at most 12, at most 13, at most 14, or at most 15. In yet other aspects of this embodiment, the number of doses administered in a multi-dose administration is from, e.g., about 2 to about 3, about 2 to about 4, about 2 to about 5, about 2 to about 6, about 3 to about 4, about 3 to about 5, about 3 to about 6, about 4 to about 5, about 4 to about 6, about 5 to about 6, about 5 to about 7, about 5 to about 8, about 5 to about 9, about 5 to about 10, about 5 to about 11, about 6 to about 7, about 6 to about 8, about 6 to about 9, about 6 to about 10, about 6 to about 11, about 7 to about 8, about 7 to about 9, about 7 to about 10, about 7 to about 11, about 8 to about 9, about 8 to about 10, about 8 to about 11, about 9 to about 10, about 9 to about 11, about 10 to about 11, about 10 to about 12, about 10 to about 13, about 10 to about 14, about 10 to about 15, about 11 to about 12, about 11 to about 13, about 11 to about 14, about 11 to about 15, about 12 to about 13, about 12 to about 14, about 12 to about 15, about 13 to about 14, about 13 to about 15, or about 14 to about 15. In still other aspects of this embodiment, the number of doses administered in a multi-dose administration is from, e.g., about 2 to about 5, about 2 to about 10, about 2 to about 15, about 5 to about 10, about 5 to about 15, or about 10 to about 15.

A multi-dose amount of a composition comprising a hyaluronidase used to effectively reduce or eliminate a hyaluronic acid-induced blockage in one or more blood vessels of an eye can include a total amount of about 15 IU to about 10,000 IU of a hyaluronidase. In aspects of this embodiment, a multi-dose amount of a composition comprising a hyaluronidase used to effectively reduce or eliminate a hyaluronic acid-induced blockage in one or more blood vessels of an eye can include a total amount of hyaluronidase that is, e.g., at least 15 IU, at least 25 IU, at least 50 IU, at least 100 IU, at least 200 IU, at least 300 IU, at least 450 IU, at least 600 IU, at least 900 IU, at least 1,000 IU, at least 1,250 IU, at least 1,500 IU, at least 1,750 IU, at least 2,000 IU, at least 3,000 IU, at least 4,000 IU, at least 5,000 IU, at least 6,000 IU, at least 7,000 IU, at least 8,000 IU, at least 9,000 IU, at least 10,000 IU, at least 11,000 IU, at least 12,000 IU, at least 13,000 IU, at least 14,000 IU, at least 15,000 IU, at least 16,000 IU, at least 17,000 IU, at least 18,000 IU, at least 19,000 IU, or at least 20,000 IU. In other aspects of this embodiment, a multi-dose amount of a composition comprising a hyaluronidase used to effectively reduce or eliminate a hyaluronic acid-induced blockage in one or more blood vessels of an eye can include a total amount of hyaluronidase that is, e.g., at most 15 IU, at most 25 IU, at most 50 IU, at most 100 IU, at most 200 IU, at most 300 IU, at most 450 IU, at most 600 IU, at most 900 IU, at most 1,000 IU, at most 1,250 IU, at most 1,500 IU, at most 1,750 IU, at most 2,000 IU, at most 3,000 IU, at most 4,000 IU, at most 5,000 IU, at most 6,000 IU, at most 7,000 IU, at most 8,000 IU, at most 9,000 IU, or at most 10,000 IU.

In yet other aspects of this embodiment, a multi-dose amount of a composition comprising a hyaluronidase used to effectively reduce or eliminate a hyaluronic acid-induced blockage in one or more blood vessels of an eye can include a total amount of hyaluronidase that is, e.g., about 15 IU to about 25 IU, about 15 IU to about 50 IU, about 15 IU to about 100 IU, about 15 IU to about 200 IU, about 15 IU to about 300 IU, about 15 IU to about 400 IU, about 15 IU to about 450 IU, about 15 IU to about 600 IU, about 15 IU to about 750 IU, about 15 IU to about 900 IU, about 25 IU to about 50 IU, about 25 IU to about 100 IU, about 25 IU to about 200 IU, about 25 IU to about 300 IU, about 25 IU to about 400 IU, about 25 IU to about 450 IU, about 25 IU to about 600 IU, about 25 IU to about 750 IU, about 25 IU to about 900 IU, about 50 IU to about 100 IU, about 50 IU to about 200 IU, about 50 IU to about 300 IU, about 50 IU to about 400 IU, about 50 IU to about 450 IU, about 50 IU to about 600 IU, about 50 IU to about 750 IU, about 50 IU to about 900 IU, about 100 IU to about 200 IU, about 100 IU to about 300 IU, about 100 IU to about 400 IU, about 100 IU to about 450 IU, about 100 IU to about 600 IU, about 100 IU to about 750 IU, about 100 IU to about 900 IU, about 200 IU to about 300 IU, about 200 IU to about 400 IU, about 200 IU to about 450 IU, about 200 IU to about 600 IU, about 200 IU to about 750 IU, about 200 IU to about 900 IU, about 300 IU to about 450 IU, about 300 IU to about 600 IU, about 300 IU to about 750 IU, about 300 IU to about 900 IU, about 450 IU to about 750 IU, about 450 IU to about 900 IU, about 450 IU to about 1,000 IU, about 450 IU to about 1,250 IU, about 600 IU to about 750 IU, about 600 IU to about 900 IU, about 600 IU to about 1,000 IU, about 600 IU to about 1,250 IU, about 600 IU to about 1,500 IU, about 750 IU to about 900 IU, about 750 IU to about 1,000 IU, about 750 IU to about 1,250 IU, about 750 IU to about 1,500 IU, about 750 IU to about 1,750 IU, about 900 IU to about 1,000 IU, about 900 IU to about 1,250 IU, about 900 IU to about 1,500 IU, about 900 IU to about 1,750 IU, about 900 IU to about 2,000 IU, about 1,000 IU to about 1,250 IU, about 1,000 IU to about 1,500 IU, about 1,000 IU to about 1,750 IU, about 1,000 IU to about 2,000 IU, about 1,000 IU to about 3,000 IU, about 1,000 IU to about 4,000 IU, about 1,000 IU to about 5,000 IU, about 1,000 IU to about 6,000 IU, about 1,000 IU to about 7,000 IU, about 1,000 IU to about 8,000 IU, about 1,000 IU to about 9,000 IU, about 1,000 IU to about 10,000 IU, about 2,000 IU to about 3,000 IU, about 2,000 IU to about 4,000 IU, about 2,000 IU to about 5,000 IU, about 2,000 IU to about 6,000 IU, about 2,000 IU to about 7,000 IU, about 2,000 IU to about 8,000 IU, about 2,000 IU to about 9,000 IU, about 2,000 IU to about 10,000 IU, about 2,500 IU to about 3,000 IU, about 2,500 IU to about 4,000 IU, about 2,500 IU to about 5,000 IU, about 2,500 IU to about 6,000 IU, about 2,500 IU to about 7,000 IU, about 2,500 IU to about 8,000 IU, about 2,500 IU to about 9,000 IU, about 2,500 IU to about 10,000 IU, about 3,000 IU to about 4,000 IU, about 3,000 IU to about 5,000 IU, about 3,000 IU to about 6,000 IU, about 3,000 IU to about 7,000 IU, about 3,000 IU to about 8,000 IU, about 3,000 IU to about 9,000 IU, about 3,000 IU to about 10,000 IU, about 4,000 IU to about 5,000 IU, about 4,000 IU to about 6,000 IU, about 4,000 IU to about 7,000 IU, about 4,000 IU to about 8,000 IU, about 4,000 IU to about 9,000 IU, about 4,000 IU to about 10,000 IU, about 5,000 IU to about 6,000 IU, about 5,000 IU to about 7,000 IU, about 5,000 IU to about 8,000 IU, about 5,000 IU to about 9,000 IU, about 5,000 IU to about 10,000 IU, about 6,000 IU to about 7,000 IU, about 6,000 IU to about 8,000 IU, about 6,000 IU to about 9,000 IU, about 6,000 IU to about 10,000 IU, about 7,000 IU to about 8,000 IU, about 7,000 IU to about 9,000 IU, about 7,000 IU to about 10,000 IU, about 8,000 IU to about 9,000 IU, about 8,000 IU to about 10,000 IU, or about 9,000 IU to about 10,000 IU.

A composition comprising a hyaluronidase disclosed herein is formulated to rapidly cover the relatively large area of a suprachoroidal space of an eye. Such rapid expansion ensures that sufficient amounts of a hyaluronidase are transported to one or more blood vessels supplying an eye within about 90 minutes or less. In aspects of this embodiment, a composition comprising a hyaluronidase disclosed herein is formulated to rapidly cover the relatively large area of a suprachoroidal space of an eye in, e.g., at most 15 minutes, at most 30 minutes, at most 45 minutes, at most 60 minutes, at most 75 minutes or at most 90 minutes. In other aspects of this embodiment, a composition comprising a hyaluronidase disclosed herein is formulated to rapidly cover the relatively large area of a suprachoroidal space of an eye in, e.g., about 5 minutes to about 10 minutes, about 5 minutes to about 15 minutes, about 5 minutes to about 30 minutes, about 10 minutes to about 15 minutes, about 10 minutes to about 30 minutes, about 15 minutes to about 30 minutes, about 15 minutes to about 45 minutes, about 15 minutes to about 60 minutes, about 15 minutes to about 75 minutes, or about 15 minutes to about 90 minutes.

In some embodiments, the rapid expansion ensures that sufficient amounts of a hyaluronidase are transported to one or more blood vessels supplying an eye within about 5 to about 15 minutes or less. In aspects of this embodiment, a composition comprising a hyaluronidase disclosed herein is formulated to rapidly cover the relatively large area of a suprachoroidal space of an eye in, e.g., at most 1 minute, at most 2 minutes, at most 3 minutes, at most 4 minutes, at most 5 minutes, at most 10 minutes, or at most 15 minutes. In other aspects of this embodiment, a composition comprising a hyaluronidase disclosed herein is formulated to rapidly cover the relatively large area of a suprachoroidal space of an eye in, e.g., about 1 minute to about 3 minutes, about 1 minute to about 5 minutes, about 1 minute to about 7 minutes, about 1 minute to about 10 minutes, about 1 minute to about 15 minutes, about 3 minutes to about 5 minutes, about 3 minutes to about 7 minutes, about 3 minutes to about 10 minutes, about 3 minutes to about 15 minutes, about 5 minutes to about 7 minutes, about 5 minutes to about 10 minutes, about 5 minutes to about 15 minutes, or about 10 minutes to about 15 minutes.

The volume of a composition comprising a hyaluronidase delivered to a suprachoroidal space can range from about 5 µL to about 500 µL. In aspects of this embodiment, a volume of a composition comprising a hyaluronidase delivered to a suprachoroidal space can be, e.g., at least 5 µL, at least 10 µL, at least 20 µL, at least 30 µL, at least 40 µL, at least 50 µL, at least 75 µL, at least 100 µL, at least 200 µL, at least 300 µL, at least 400 µL, or at least 500 µL. In other aspects of this embodiment, a volume of a composition comprising a hyaluronidase delivered to a suprachoroidal space can be, e.g., at most 5 µL, at most 10 µL, at most 20 µL, at most 30 µL, at most 40 µL, at most 50 µL, at most 75 µL, at most 100 µL, at most 200 µL, at most 300 µL, at most 400 µL, or at most 500 µL. In yet other aspects of this embodiment, a volume of a composition comprising a hyaluronidase delivered to a suprachoroidal space can be, e.g., about 5 µL to about 25 µL, about 5 µL to about 50 µL, about 5 µL to about 75 µL, about 5 µL to about 100 µL, about 10 µL to about 25 µL, about 10 µL to about 50 µL, about 10 µL to about 75 µL, about 10 µL to about 100 µL, about 25 µL to about 50 µL, about 25 µL to about 75 µL, about 25 µL to about 100 µL, about 25 µL to about 150 µL, about 50 µL to about 75 µL, about 50 µL to about 100 µL, about 50 µL to about 150 µL, about 50 µL to about 200 µL, about 50 µL to about 250 µL, about 100 µL to about 150 µL, about 100 µL to about 200 µL, about 100 µL to about 250 µL, about 100 µL to about 300 µL, about 100 µL to about 400 µL, about 100 µL to about 500 µL, about 200 µL to about 300 µL, about 200 µL to about 400 µL, about 200 µL to about 500 µL, about 300 µL to about 400 µL, about 300 µL to about 500 µL, or about 400 µL to about 500 µL.

Aspects of the present specification disclose a delivery system. Non-limiting examples of a delivery system include such as, e.g., a needle and syringe, ADG needle, an ADG-like needle, or a microinjector. Non-limiting examples of needle gauged useful for a delivery system, such as, e.g., a needle and syringe, ADG needle, an ADG-like needle, or a microinjector, include 21 gauge, 22 gauge, 23 gauge, 24 gauge, 25 gauge, 26 gauge, 27 gauge, 28 gauge, 29 gauge, 30 gauge, 31 gauge, 32 gauge, and 33 gauge.

Figure 5:
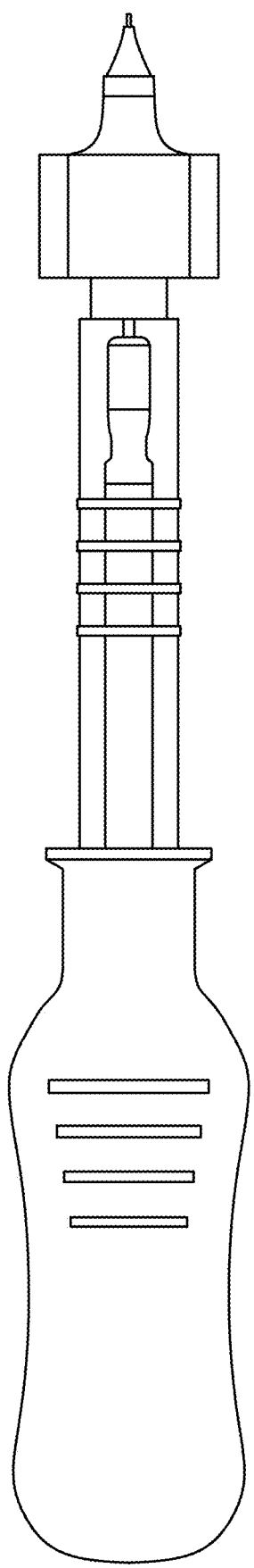
FIG. 5 illustrates a microinjector.

Other aspects of the present specification disclose a microinjector. A non-limiting example of a microinjector includes a suprachoroidal microinjector. A composition comprising a hyaluronidase disclosed herein can be administered to a suprachoroidal space of an eye using a microinjector (FIG. 5). Such microinjectors are commercially available and include, without limitation, a SCS™ Microinjector (Clearside Biomedical Inc., Alpharetta, Ga.).

Aspects of the present specification disclose a suprachoroidal space. A suprachoroidal space is the space between the choroid and the sclera that traverses the circumference of the posterior segment of an eye. A suprachoroidal space facilitates easy access to the choroid, retinal pigment epithelium, and retina.

Suprachoroidal dosing of a composition comprising a hyaluronidase for the treatment of ophthalmic vascular occlusion has several potential advantages, including high bioavailability as well as differentiating efficacy and safety. Suprachoroidal administration gives access to posterior tissues of the eye. As shown in FIGS. 6A-D, suprachoroidally injected fluids rapidly cover a relatively large area, as much as a few square centimeters, within a few seconds of administration. In addition, hyaluronidase distribution is predominantly in the retina and choroid with low amounts of the enzyme entering in the anterior segment of the eye, resulting in lower incidence of IOP (intraocular pressure) increases and cataract formation. Suprachoroidal administration is also an attractive route of hyaluronidase delivery because it allows for the bypassing of the sclera without the risk of intraocular penetration. Besides keeping systemic levels of hyaluronidase low, suprachoroidal administration also facilitates using lower amounts of hyaluronidase when compared to intravitreal or other ophthalmic delivery routes.

Aspects of the present specification disclose methods of reducing or eliminating a hyaluronic acid-induced blockage in one or more blood vessels supplying blood to an eye. The disclosed methods comprise administering a composition comprising a hyaluronidase to an individual in a manner that reduces or eliminates a hyaluronic acid-induced blockage in one or more blood vessels supplying blood to an eye. In aspects, the disclosed methods administer composition comprising a hyaluronidase to a suprachoroidal space of an eye. In other aspects, the disclosed methods administer a composition comprising a hyaluronidase using a delivery system disclosed herein. The disclosed methods can administer a composition comprising a hyaluronidase in a single- or multi-dose amount ranging from about 15 IU to about 10,000 IU of a hyaluronidase.

In aspects of this embodiment, reducing or eliminating a hyaluronic acid-induced blockage in one or more blood vessels supplying blood to an eye reduces or inhibits one or more physiological conditions or symptoms associated with a hyaluronic acid-induced blockage in one or more blood vessels of an eye by, e.g., at least 10%, at least 20%, at least 30%, at least 40%, at least 50%, at least 60%, at least 70%, at least 80%, at least 90% or at least 95% or more. In other aspects of this embodiment, reducing or eliminating a hyaluronic acid-induced blockage in one or more blood vessels supplying blood to an eye reduces or inhibits one or more physiological conditions or symptoms associated with a hyaluronic acid-induced blockage in one or more blood vessels of an eye by, e.g., at most 10%, at most 20%, at most 30%, at most 40%, at most 50%, at most 60%, at most 70%, at most 80%, at most 90% or at most 100%. In yet other aspects of this embodiment, reducing or eliminating a hyaluronic acid-induced blockage in one or more blood vessels supplying blood to an eye reduces or inhibits one or more physiological conditions or symptoms associated with a hyaluronic acid-induced blockage in one or more blood vessels of an eye by, e.g., about 10% to about 100%, about 10% to about 90%, about 10% to about 80%, about 10% to about 70%, about 10% to about 60%, about 10% to about 50%, about 10% to about 40%, about 10% to about 30%, about 10% to about 20%, about 20% to about 100%, about 20% to about 90%, about 20% to about 80%, about 20% to about 70%, about 20% to about 60%, about 20% to about 50%, about 20% to about 40%, about 20% to about 30%, about 30% to about 100%, about 30% to about 90%, about 30% to about 80%, about 30% to about 70%, about 30% to about 60%, about 30% to about 50%, about 30% to about 40%, about 40% to about 100%, about 40% to about 90%, about 40% to about 80%, about 40% to about 70%, about 40% to about 60%, about 40% to about 50%, about 50% to about 100%, about 50% to about 90%, about 50% to about 80%, about 50% to about 70%, about 50% to about 60%, about 60% to about 100%, about 60% to about 90%, about 60% to about 80%, about 60% to about 70%, about 70% to about 100%, about 70% to about 90%, about 70% to about 80%, about 80% to about 100%, about 80% to about 90%, or about 90% to about 100%. In still other aspects of this embodiment, reducing or eliminating a hyaluronic acid-induced blockage in one or more blood vessels supplying blood to an eye reduces or inhibits one or more physiological conditions or symptoms associated with a hyaluronic acid-induced blockage in one or more blood vessels of an eye for, e.g., at least one week, at least one month, at least two months, at least three months, at least four months, at least five months, at least six months, at least seven months, at least eight months, at least nine months, at least ten months, at least eleven months, or at least twelve months.

Aspects of the present specification disclose methods of reducing or inhibiting a vascular occlusion in an eye of an individual in need thereof. A vascular occlusion is reduced or inhibited by reducing or eliminating a hyaluronic acid-induced blockage in one or more blood vessels supplying blood to the eye.

The disclosed methods comprise administering a composition comprising a hyaluronidase to an individual in a manner that reduces or eliminates a hyaluronic acid-induced blockage in one or more blood vessels supplying blood to an eye, thereby reducing or inhibiting the vascular occlusion in the eye. In aspects, the disclosed methods administer composition comprising a hyaluronidase to a suprachoroidal space of an eye. In other aspects, the disclosed methods administer a composition comprising a hyaluronidase using a microinjector. The disclosed methods can administer a composition comprising a hyaluronidase in a single- or multi-dose amount ranging from about 15 IU to about 10,000 IU of a hyaluronidase.

In aspects of this embodiment, reducing or inhibiting a vascular occlusion in an eye reduces or inhibits one or more physiological conditions or symptoms associated with a hyaluronic acid-induced blockage in one or more blood vessels of an eye by, e.g., at least 10%, at least 20%, at least 30%, at least 40%, at least 50%, at least 60%, at least 70%, at least 80%, at least 90% or at least 100%. In other aspects of this embodiment, reducing or inhibiting a vascular occlusion in an eye reduces or inhibits one or more physiological conditions or symptoms associated with a hyaluronic acid-induced blockage in one or more blood vessels of an eye by, e.g., at most 10%, at most 20%, at most 30%, at most 40%, at most 50%, at most 60%, at most 70%, at most 80%, at most 90% or at most 100%. In yet other aspects of this embodiment, reducing or inhibiting a vascular occlusion in an eye reduces or inhibits one or more physiological conditions or symptoms associated with a hyaluronic acid-induced blockage in one or more blood vessels of an eye by, e.g., about 10% to about 100%, about 10% to about 90%, about 10% to about 80%, about 10% to about 70%, about 10% to about 60%, about 10% to about 50%, about 10% to about 40%, about 10% to about 30%, about 10% to about 20%, about 20% to about 100%, about 20% to about 90%, about 20% to about 80%, about 20% to about 70%, about 20% to about 60%, about 20% to about 50%, about 20% to about 40%, about 20% to about 30%, about 30% to about 100%, about 30% to about 90%, about 30% to about 80%, about 30% to about 70%, about 30% to about 60%, about 30% to about 50%, about 30% to about 40%, about 40% to about 100%, about 40% to about 90%, about 40% to about 80%, about 40% to about 70%, about 40% to about 60%, about 40% to about 50%, about 50% to about 100%, about 50% to about 90%, about 50% to about 80%, about 50% to about 70%, about 50% to about 60%, about 60% to about 100%, about 60% to about 90%, about 60% to about 80%, about 60% to about 70%, about 70% to about 100%, about 70% to about 90%, about 70% to about 80%, about 80% to about 100%, about 80% to about 90%, or about 90% to about 100%. In still other aspects of this embodiment, reducing or inhibiting a vascular occlusion in an eye reduces or inhibits one or more physiological conditions or symptoms associated with a hyaluronic acid-induced blockage in one or more blood vessels of an eye for, e.g., at least one week, at least one month, at least two months, at least three months, at least four months, at least five months, at least six months, at least seven months, at least eight months, at least nine months, at least ten months, at least eleven months, or at least twelve months.

Aspects of the present specification disclose methods of reducing or inhibiting hyaluronic acid-induced loss of vision in an individual in need thereof. A hyaluronic acid-induced loss of vision is reduced or inhibited by reducing or eliminating a hyaluronic acid-induced blockage in one or more blood vessels supplying blood to an eye. The disclosed methods comprise administering a composition comprising a hyaluronidase to an individual in a manner that reduces or eliminates a hyaluronic acid-induced blockage in one or more blood vessels supplying blood to an eye, thereby reducing or inhibiting the hyaluronic acid-induced loss of vision in the individual. In aspects, the disclosed methods administer a composition comprising a hyaluronidase to a suprachoroidal space of an eye. In other aspects, the disclosed methods administer a composition comprising a hyaluronidase using a delivery system disclosed herein. The disclosed methods can administer a composition comprising a hyaluronidase in a single- or multi-dose amount ranging from about 15 IU to about 10,000 IU of a hyaluronidase.

In some embodiments, when the methods disclosed herein comprise multiple doses of a hyaluronidase, such administrations can occur in rapid succession. In aspects of these embodiments, 3 to 20 doses of a composition comprising a hyaluronidase can be administered to the same eye within 5 to 15 minutes. In other aspects of these embodiments, 5 to 15 doses of a composition comprising a hyaluronidase can be administered to the same eye within 5 to 15 minutes. In yet other aspects of these embodiments, 7 to 15 doses of a composition comprising a hyaluronidase can be administered to the same eye within 5 to 15 minutes. In still other aspects of these embodiments, 8 to 12 doses of a composition comprising a hyaluronidase can be administered to the same eye within 5 to 15 minutes. In still other aspects of these embodiments, 10 doses of a composition comprising a hyaluronidase can be administered to the same eye within 5 to 15 minutes.

In aspects of this embodiment, reducing or eliminating a hyaluronic acid-induced blockage in one or more blood vessels supplying blood to an eye restores or maintains one or more qualitative or quantitative aspects of vision by, e.g., at least 10%, at least 20%, at least 30%, at least 40%, at least 50%, at least 60%, at least 70%, at least 80%, at least 90% or at least 100%. In other aspects of this embodiment, reducing or eliminating a hyaluronic acid-induced blockage in one or more blood vessels supplying blood to an eye restores or maintains one or more qualitative or quantitative aspects of vision by, e.g., at most 10%, at most 20%, at most 30%, at most 40%, at most 50%, at most 60%, at most 70%, at most 80%, at most 90% or at most 100%. In yet other aspects of this embodiment, reducing or eliminating a hyaluronic acid-induced blockage in one or more blood vessels supplying blood to an eye restores or maintains one or more qualitative or quantitative aspects of vision by, e.g., about 10% to about 100%, about 10% to about 90%, about 10% to about 80%, about 10% to about 70%, about 10% to about 60%, about 10% to about 50%, about 10% to about 40%, about 10% to about 30%, about 10% to about 20%, about 20% to about 100%, about 20% to about 90%, about 20% to about 80%, about 20% to about 70%, about 20% to about 60%, about 20% to about 50%, about 20% to about 40%, about 20% to about 30%, about 30% to about 100%, about 30% to about 90%, about 30% to about 80%, about 30% to about 70%, about 30% to about 60%, about 30% to about 50%, about 30% to about 40%, about 40% to about 100%, about 40% to about 90%, about 40% to about 80%, about 40% to about 70%, about 40% to about 60%, about 40% to about 50%, about 50% to about 100%, about 50% to about 90%, about 50% to about 80%, about 50% to about 70%, about 50% to about 60%, about 60% to about 100%, about 60% to about 90%, about 60% to about 80%, about 60% to about 70%, about 70% to about 100%, about 70% to about 90%, about 70% to about 80%, about 80% to about 100%, about 80% to about 90%, or about 90% to about 100%. In still other aspects of this embodiment, reducing or eliminating a hyaluronic acid-induced blockage in one or more blood vessels supplying blood to an eye restores or maintains one or more qualitative or quantitative aspects of vision for, e.g., at least one week, at least one month, at least two months, at least three months, at least four months, at least five months, at least six months, at least seven months, at least eight months, at least nine months, at least ten months, at least eleven months, or at least twelve months.

Figure 6A:
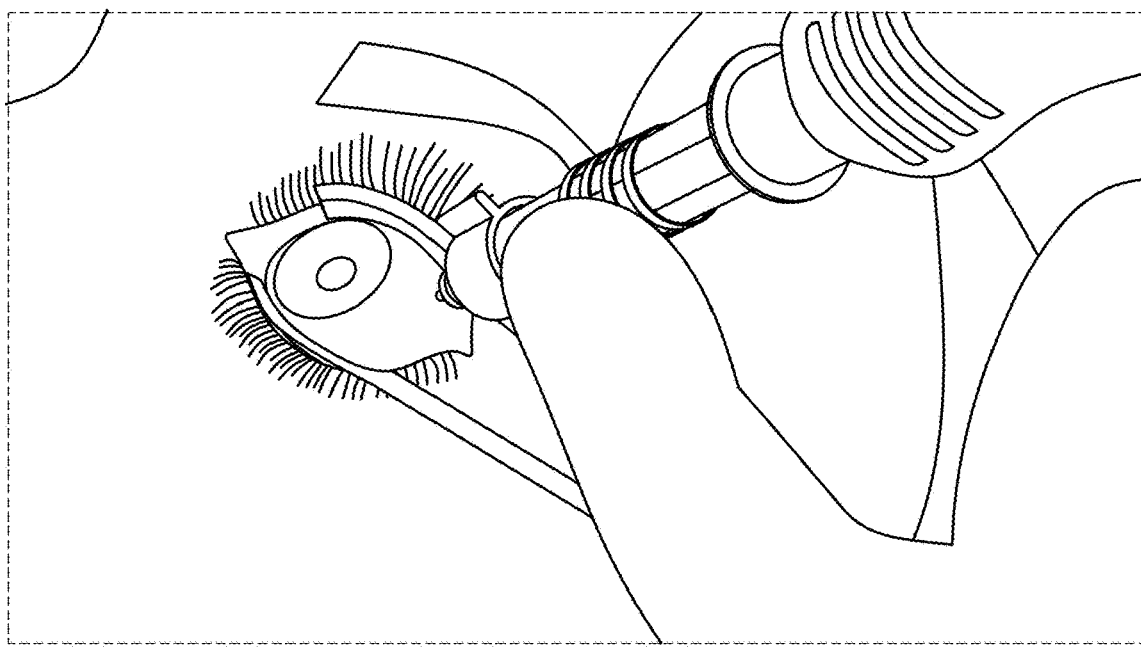
FIG. 6A-D illustrates administration of a composition comprising a hyaluronidase to a suprachoroidal space of an eye using a microinjector, with FIG. 6A showing general location of injection site.
Figure 6B:
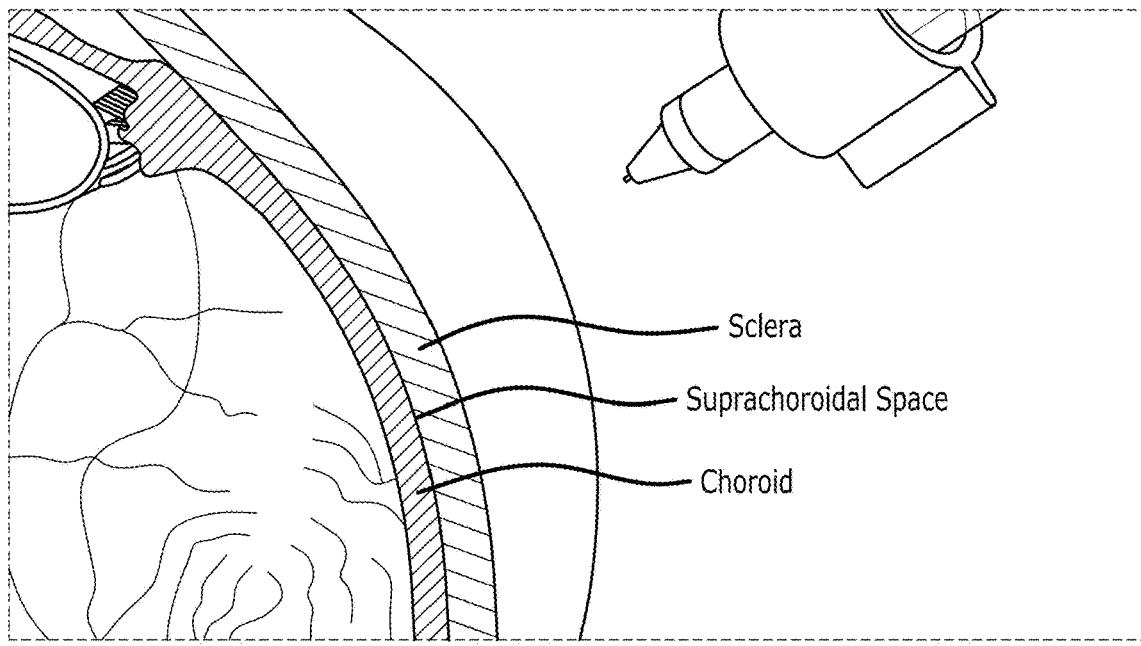
Figure 6C:
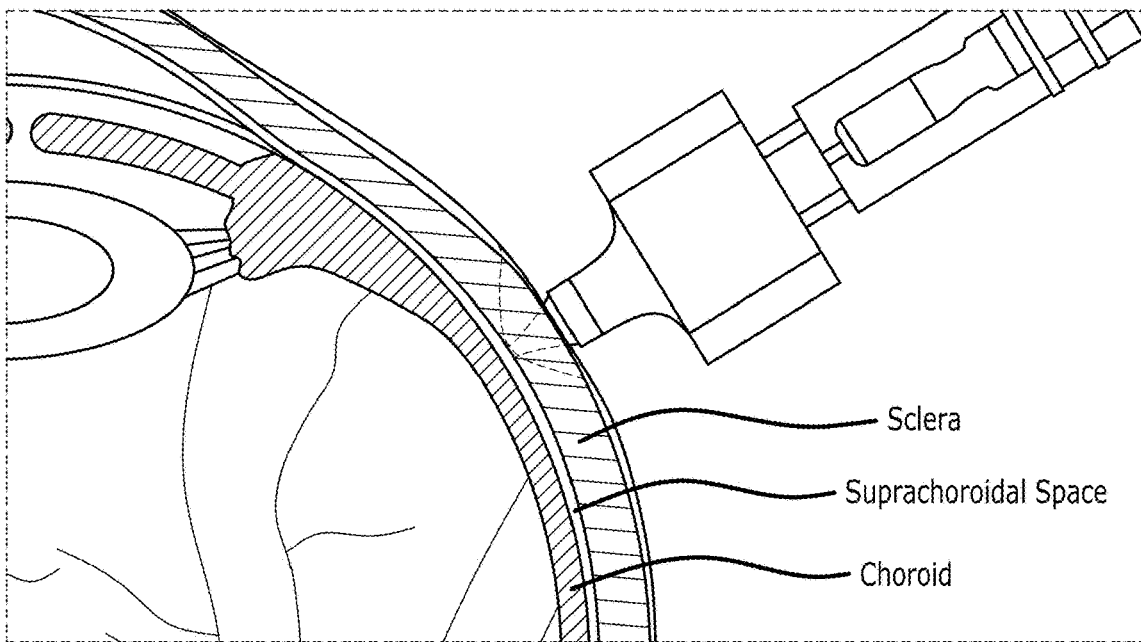
Figure 6D:
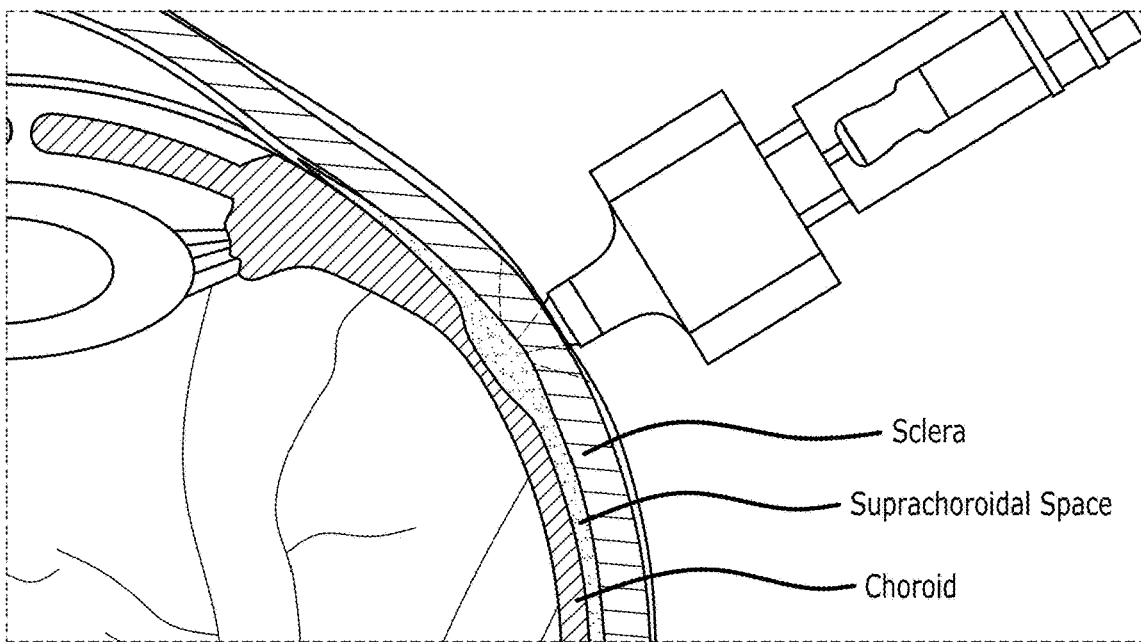

In one embodiment, as shown in FIGS. 6A-D, composition comprising a hyaluronidase can be administered to the suprachoroidal space. Referring to FIGS. 6A-B, a delivery system, depicted as a microinjector, is position over a portion of the sclera with the device perpendicular to the surface of the injection site. Referring now to FIG. 6C, the device is then pressed against the scleral surface to create a "dimple" around the hub of the delivery system. As shown in FIG. 6D, the needle of the delivery system is then inserted through the scleral layer and into the suprachoroidal space, and the plunger of the device is depressed gently while maintaining the dimple on the eye surface for 3-5 seconds to completely administer the hyaluronidase into the suprachoroidal space. Administration can be completed with one or two hands, depending on the user's preference.

The methods disclosed herein reduce or eliminate a hyaluronic acid-induced blockage in one or more blood vessels supplying blood to an eye. In some embodiments, the methods disclosed herein reduce or eliminate a hyaluronic acid-induced blockage in one or more blood vessels supplying blood to an eye within a timeframe that prevents, reduces or stops loss of vision or other organ or tissue damage.

In some embodiments, the methods disclosed herein reduce or eliminate a hyaluronic acid-induced blockage in one or more blood vessels supplying blood to an eye within about 90 minutes or less. In aspects of this embodiment, a hyaluronic acid-induced blockage in one or more blood vessels supplying blood to an eye is reduced or eliminated in, e.g., at most 15 minutes, at most 30 minutes, at most 45 minutes, at most 60 minutes, at most 75 minutes or at most 90 minutes. In other aspects of this embodiment, a hyaluronic acid-induced blockage in one or more blood vessels supplying blood to an eye is reduced or eliminated in, e.g., about 5 minutes to about 10 minutes, about 5 minutes to about 15 minutes, about 5 minutes to about 30 minutes, about 10 minutes to about 15 minutes, about 10 minutes to about 30 minutes, about 15 minutes to about 30 minutes, about 15 minutes to about 45 minutes, about 15 minutes to about 60 minutes, about 15 minutes to about 75 minutes, about 15 minutes to about 90 minutes.

In some embodiments, the methods disclosed herein reduce or eliminate a hyaluronic acid-induced blockage in one or more blood vessels supplying blood to an eye within about 5 to about 15 minutes or less. In aspects of this embodiment, a hyaluronic acid-induced blockage in one or more blood vessels supplying blood to an eye is reduced or eliminated in, e.g., at most 1 minute, at most 2 minutes, at most 3 minutes, at most 4 minutes, at most 5 minutes, at most 10 minutes, or at most 15 minutes. In other aspects of this embodiment, a hyaluronic acid-induced blockage in one or more blood vessels supplying blood to an eye is reduced or eliminated in, e.g., about 1 minute to about 3 minutes, about 1 minute to about 5 minutes, about 1 minute to about 7 minutes, about 1 minute to about 10 minutes, about 1 minute to about 15 minutes, about 3 minutes to about 5 minutes, about 3 minutes to about 7 minutes, about 3 minutes to about 10 minutes, about 3 minutes to about 15 minutes, about 5 minutes to about 7 minutes, about 5 minutes to about 10 minutes, about 5 minutes to about 15 minutes, or about 10 minutes to about 15 minutes.

Aspects of the present specification disclose a kit. In one embodiment, the kit can comprise a container that includes a composition comprising a hyaluronidase disclosed herein. In another embodiment, a kit can comprise a plurality of containers, with each such container including a composition comprising a hyaluronidase disclosed herein. For example, a kit can comprise 1, 2, 3, 4, 5, 6, 7, 8, 9, 10, 11, 12, 13, 14, 15, 16, 17, 18, 19 or 20 or more containers, with each such container including a composition comprising a hyaluronidase disclosed herein. Each of the disclosed containers can comprise a single dose of a composition comprising a hyaluronidase disclosed herein, multiple doses of a composition comprising a hyaluronidase disclosed herein, or a combination thereof. In addition, each of the disclosed containers can contain a composition comprising a hyaluronidase disclosed herein in liquid form or in dried form.

In some embodiments, a container disclosed herein can be a vial or similar vessel containing a composition comprising a hyaluronidase disclosed herein, where such composition comprising a hyaluronidase disclosed herein would need to be transferred to a delivery system, such as, e.g., a needle and syringe, ADG needle, or a microinjector. In some embodiments, a kit can comprise one or more vials, e.g., 7 to 15 vials or 8 to 12 vials or 10 vials, with each such vial containing a composition comprising a hyaluronidase disclosed herein and optionally one or more delivery systems, e.g., 7 to 15 delivery systems or 8 to 12 delivery systems or 10 delivery systems, with each such delivery system employed to deliver the disclosed compositions when needed.

In some embodiments, a container disclosed herein can be a delivery system containing a composition comprising a hyaluronidase disclosed herein. In some embodiments, a kit can comprise one or more delivery systems, e.g., 7 to 15 delivery systems or 8 to 12 delivery systems or 10 delivery systems, with each such delivery system containing a composition comprising a hyaluronidase disclosed herein. In aspects of this embodiment, a kit can comprise one or more microinjectors, e.g., 7 to 15 microinjectors or 8 to 12 microinjectors or 10 microinjectors, with each such microinjector containing a composition comprising a hyaluronidase disclosed herein. In aspects of this embodiment, a kit can comprise one or more ADG needles, e.g., 7 to 15 ADG needles or 8 to 12 ADG needles or 10 ADG needles, with each such ADG needle containing a composition comprising a hyaluronidase disclosed herein.

A kit disclosed herein can comprise other components. For example, a kit disclosed herein can further include containers comprising a solvent, such as, e.g., water or a buffered solution, e.g. saline. A solvent disclosed herein is useful to reconstitute a dried pharmaceutical composition disclosed herein.

A kit disclosed herein can comprise a delivery system. The delivery system of the kit is useful for applying a composition disclosed herein to a site of interest, e.g., a suprachoroidal space disclosed herein.

A delivery or application system disclosed herein includes, without limitation, one or more needles, syringes, ADG needles, and/or microinjectors. In an embodiment, a kit comprises a single delivery system. In another embodiment, a kit comprises a plurality of delivery systems. For example, each kit can comprise 2, 3, 4, 5, 6, 7, 8, 9, 10, 11, 12, 13, 14, 15, 16, 17, 18, 19 or 20 or more delivery systems. Within the kit, the delivery system may be packaged individually or in sets of 2 or more. The delivery system can be packaged such that it remains sterile until use. In certain embodiments, a delivery system disclosed herein can be packaged in plastic sheaths. Further, to prevent contamination, a delivery system disclosed herein is preferably a single-use, disposable delivery system.

The kit can also comprise a set of instructions. The instructions may include information useful to the end user such as, e.g., how to use a delivery system to apply a composition disclosed herein and/or how often to apply a composition disclosed herein. In addition, such instructions may include information regarding how to mix a solvent disclosed herein to reconstitute a dried composition disclosed herein. Such instructions can indicate that mixing should be done at a certain time before application, e.g., just prior to use. Instructions disclosed herein may also include information regarding how to apply a composition disclosed herein directly to a site of interest, e.g., a suprachoroidal space disclosed herein, and in what order or timing the composition disclosed herein should be applied to such sites of interest.

The contents of the kit, including a container, a composition, a delivery system, and instructions disclosed herein, are enclosed in an outer casing. The outer casing can be a box, a sealed bag, a foil pouch, etc. In certain embodiments, the delivery system, container and instructions are enclosed in a box. In other embodiments of the kit, the container and instructions are contained in a first box, the delivery system is contained in a second box, and the first and second boxes are contained together in a third box.

Aspects of the present specification can also be described according to the following embodiments:

1. A method of reducing or eliminating a hyaluronic acid-induced blockage in one or more blood vessels supplying blood to an eye in an individual in need thereof, the method comprising administering a composition comprising a hyaluronidase to the individual in a manner that reduces or eliminates a hyaluronic acid-induced blockage in one or more blood vessels supplying blood to an eye.
2. A method of reducing or inhibiting a vascular occlusion in an eye of an individual in need thereof, the method comprising administering a composition comprising a hyaluronidase to the individual in a manner that reduces or eliminates a hyaluronic acid-induced blockage in one or more blood vessels supplying blood to an eye, thereby reducing or inhibiting the vascular occlusion in the eye.
3. A method of reducing or inhibiting a hyaluronic acid-induced loss of vision in an individual in need thereof, the method comprising administering a composition comprising a hyaluronidase to an individual in a manner that reduces or eliminates a hyaluronic acid-induced blockage in one or more blood vessels supplying blood to an eye, thereby reducing or inhibiting the hyaluronic acid-induced loss of vision in the individual.
4. The method according to any one of embodiments 1-3, wherein the composition is administered to a suprachoroidal space of the eye.
5. The method according to any one of embodiments 1-4, wherein the composition is administered using a delivery system.
6. The method according to any one of embodiments 1-5, wherein the composition comprises the hyaluronidase in a concentration of at least 15 IU/mL, at least 25 IU/mL, at least 50 IU/mL, at least 100 IU/mL, at least 200 IU/mL, at least 300 IU/mL, at least 450 IU/mL, at least 600 IU/mL, at least 900 IU/mL, at least 1,000 IU/mL, at least 1,250 IU/mL, at least 1,500 IU/mL, at least 1,750 IU/mL, at least 2,000 IU/mL, at least 3,000 IU/mL, at least 4,000 IU/mL, at least 5,000 IU/mL, at least 6,000 IU/mL, at least 7,000 IU/mL, at least 8,000 IU/mL, at least 9,000 IU/mL, at least 10,000 IU/mL, at least 11,000 IU/mL, at least 12,000 IU/mL, at least 13,000 IU/mL, at least 14,000 IU/mL, at least 15,000 IU/mL, at least 16,000 IU/mL, at least 17,000 IU/mL, at least 18,000 IU/mL, at least 19,000 IU/mL, or at least 20,000 IU/mL; and/or in an amount of at most 15 IU/mL, at most 25 IU/mL, at most 50 IU/mL, at most 100 IU/mL, at most 200 IU/mL, at most 300 IU/mL, at most 450 IU/mL, at most 600 IU/mL, at most 900 IU/mL, at most 1,000 IU/mL, at most 1,250 IU/mL, at most 1,500 IU/mL, at most 1,750 IU/mL, at most 2,000 IU/mL, at most 3,000 IU/mL, at most 4,000 IU/mL, at most 5,000 IU/mL, at most 6,000 IU/mL, at most 7,000 IU/mL, at most 8,000 IU/mL, at most 9,000 IU/mL, at most 10,000 IU/mL, at most 11,000 IU/mL, at most 12,000 IU/mL, at most 13,000 IU/mL, at most 14,000 IU/mL, at most 15,000 IU/mL, at most 16,000 IU/mL, at most 17,000 IU/mL, at most 18,000 IU/mL, at most 19,000 IU/mL, or at most 20,000 IU/mL; or in an amount of about 15 IU/mL to about 25 IU/mL, about 15 IU/mL to about 50 IU/mL, about 15 IU/mL to about 100 IU/mL, about 15 IU/mL to about 200 IU/mL, about 15 IU/mL to about 300 IU/mL, about 15 IU/mL to about 400 IU/mL, about 15 IU/mL to about 450 IU/mL, about 15 IU/mL to about 600 IU/mL, about 15 IU/mL to about 750 IU/mL, about 15 IU/mL to about 900 IU/mL, about 25 IU/mL to about 50 IU/mL, about 25 IU/mL to about 100 IU/mL, about 25 IU/mL to about 200 IU/mL, about 25 IU/mL to about 300 IU/mL, about 25 IU/mL to about 400 IU/mL, about 25 IU/mL to about 450 IU/mL, about 25 IU/mL to about 600 IU/mL, about 25 IU/mL to about 750 IU/mL, about 25 IU/mL to about 900 IU/mL, about 50 IU/mL to about 100 IU/mL, about 50 IU/mL to about 200 IU/mL, about 50 IU/mL to about 300 IU/mL, about 50 IU/mL to about 400 IU/mL, about 50 IU/mL to about 450 IU/mL, about 50 IU/mL to about 600 IU/mL, about 50 IU/mL to about 750 IU/mL, about 50 IU/mL to about 900 IU/mL, about 100 IU/mL to about 200 IU/mL, about 100 IU/mL to about 300 IU/mL, about 100 IU/mL to about 400 IU/mL, about 100 IU/mL to about 450 IU/mL, about 100 IU/mL to about 600 IU/mL, about 100 IU/mL to about 750 IU/mL, about 100 IU/mL to about 900 IU/mL, about 200 IU/mL to about 300 IU/mL, about 200 IU/mL to about 400 IU/mL, about 200 IU/mL to about 450 IU/mL, about 200 IU/mL to about 600 IU/mL, about 200 IU/mL to about 750 IU/mL, about 200 IU/mL to about 900 IU/mL, about 300 IU/mL to about 450 IU/mL, about 300 IU/mL to about 600 IU/mL, about 300 IU/mL to about 750 IU/mL, about 300 IU/mL to about 900 IU/mL, about 450 IU/mL to about 600 IU/mL, about 450 IU/mL to about 750 IU/mL, about 450 IU/mL to about 900 IU/mL, about 450 IU/mL to about 1,000 IU/mL, about 450 IU/mL to about 1,250 IU/mL, about 600 IU/mL to about 750 IU/mL, about 600 IU/mL to about 900 IU/mL, about 600 IU/mL to about 1,000 IU/mL, about 600 IU/mL to about 1,250 IU/mL, about 600 IU/mL to about 1,500 IU/mL, about 750 IU/mL to about 900 IU/mL, about 750 IU/mL to about 1,000 IU/mL, about 750 IU/mL to about 1,250 IU/mL, about 750 IU/mL to about 1,500 IU/mL, about 750 IU/mL to about 1,750 IU/mL, about 900 IU/mL to about 1,000 IU/mL, about 900 IU/mL to about 1,250 IU/mL, about 900 IU/mL to about 1,500 IU/mL, about 900 IU/mL to about 1,750 IU/mL, about 900 IU/mL to about 2,000 IU/mL, about 1,000 IU/mL to about 1,250 IU/mL, about 1,000 IU/mL to about 1,500 IU/mL, about 1,000 IU/mL to about 1,750 IU/mL, about 1,000 IU/mL to about 2,000 IU/mL, about 1,000 IU/mL to about 3,000 IU/mL, about 1,000 IU/mL to about 4,000 IU/mL, about 1,000 IU/mL to about 5,000 IU/mL, about 1,000 IU/mL to about 6,000 IU/mL, about 1,000 IU/mL to about 7,000 IU/mL, about 1,000 IU/mL to about 8,000 IU/mL, about 1,000 IU/mL to about 9,000 IU/mL, about 1,000 IU/mL to about 10,000 IU/mL, about 2,000 IU/mL to about 3,000 IU/mL, about 2,000 IU/mL to about 4,000 IU/mL, about 2,000 IU/mL to about 5,000 IU/mL, about 2,000 IU/mL to about 6,000 IU/mL, about 2,000 IU/mL to about 7,000 IU/mL, about 2,000 IU/mL to about 8,000 IU/mL, about 2,000 IU/mL to about 9,000 IU/mL, about 2,000 IU/mL to about 10,000 IU/mL, about 2,500 IU/mL to about 3,000 IU/mL, about 2,500 IU/mL to about 4,000 IU/mL, about 2,500 IU/mL to about 5,000 IU/mL, about 2,500 IU/mL to about 6,000 IU/mL, about 2,500 IU/mL to about 7,000 IU/mL, about 2,500 IU/mL to about 8,000 IU/mL, about 2,500 IU/mL to about 9,000 IU/mL, about 2,500 IU/mL to about 10,000 IU/mL, about 3,000 IU/mL to about 4,000 IU/mL, about 3,000 IU/mL to about 5,000 IU/mL, about 3,000 IU/mL to about 6,000 IU/mL, about 3,000 IU/mL to about 7,000 IU/mL, about 3,000 IU/mL to about 8,000 IU/mL, about 3,000 IU/mL to about 9,000 IU/mL, about 3,000 IU/mL to about 10,000 IU/mL, about 4,000 IU/mL to about 5,000 IU/mL, about 4,000 IU/mL to about 6,000 IU/mL, about 4,000 IU/mL to about 7,000 IU/mL, about 4,000 IU/mL to about 8,000 IU/mL, about 4,000 IU/mL to about 9,000 IU/mL, about 4,000 IU/mL to about 10,000 IU/mL, about 5,000 IU/mL to about 6,000 IU/mL, about 5,000 IU/mL to about 7,000 IU/mL, about 5,000 IU/mL to about 8,000 IU/mL, about 5,000 IU/mL to about 9,000 IU/mL, about 5,000 IU/mL to about 10,000 IU/mL, about 6,000 IU/mL to about 7,000 IU/mL, about 6,000 IU/mL to about 8,000 IU/mL, about 6,000 IU/mL to about 9,000 IU/mL, about 6,000 IU/mL to about 10,000 IU/mL, about 7,000 IU/mL to about 8,000 IU/mL, about 7,000 IU/mL to about 9,000 IU/mL, about 7,000 IU/mL to about 10,000 IU/mL, about 8,000 IU/mL to about 9,000 IU/mL, about 8,000 IU/mL to about 10,000 IU/mL, about 9,000 IU/mL to about 10,000 IU/mL, about 10,000 IU/mL to about 11,000 IU/mL, about 10,000 IU/mL to about 12,000 IU/mL, about 10,000 IU/mL to about 13,000 IU/mL, about 10,000 IU/mL to about 14,000 IU/mL, about 10,000 IU/mL to about 15,000 IU/mL, about 10,000 IU/mL to about 16,000 IU/mL, about 10,000 IU/mL to about 17,000 IU/mL, about 10,000 IU/mL to about 18,000 IU/mL, about 10,000 IU/mL to about 19,000 IU/mL, about 10,000 IU/mL to about 20,000 IU/mL, about 11,000 IU/mL to about 12,000 IU/mL, about 11,000 IU/mL to about 13,000 IU/mL, about 11,000 IU/mL to about 14,000 IU/mL, about 11,000 IU/mL to about 15,000 IU/mL, about 11,000 IU/mL to about 16,000 IU/mL, about 11,000 IU/mL to about 17,000 IU/mL, about 11,000 IU/mL to about 18,000 IU/mL, about 11,000 IU/mL to about 19,000 IU/mL, about 11,000 IU/mL to about 20,000 IU/mL, about 12,000 IU/mL to about 13,000 IU/mL, about 12,000 IU/mL to about 14,000 IU/mL, about 12,000 IU/mL to about 15,000 IU/mL, about 12,000 IU/mL to about 16,000 IU/mL, about 12,000 IU/mL to about 17,000 IU/mL, about 12,000 IU/mL to about 18,000 IU/mL, about 12,000 IU/mL to about 19,000 IU/mL, about 12,000 IU/mL to about 20,000 IU/mL, about 13,000 IU/mL to about 14,000 IU/mL, about 13,000 IU/mL to about 15,000 IU/mL, about 13,000 IU/mL to about 16,000 IU/mL, about 13,000 IU/mL to about 17,000 IU/mL, about 13,000 IU/mL to about 18,000 IU/mL, about 13,000 IU/mL to about 19,000 IU/mL, about 13,000 IU/mL to about 20,000 IU/mL, about 14,000 IU/mL to about 15,000 IU/mL, about 14,000 IU/mL to about 16,000 IU/mL, about 14,000 IU/mL to about 17,000 IU/mL, about 14,000 IU/mL to about 18,000 IU/mL, about 14,000 IU/mL to about 19,000 IU/mL, about 14,000 IU/mL to about 20,000 IU/mL, about 15,000 IU/mL to about 16,000 IU/mL, about 15,000 IU/mL to about 17,000 IU/mL, about 15,000 IU/mL to about 18,000 IU/mL, about 15,000 IU/mL to about 19,000 IU/mL, about 15,000 IU/mL to about 20,000 IU/mL, about 16,000 IU/mL to about 17,000 IU/mL, about 16,000 IU/mL to about 18,000 IU/mL, about 16,000 IU/mL to about 19,000 IU/mL, about 16,000 IU/mL to about 20,000 IU/mL, about 17,000 IU/mL to about 18,000 IU/mL, about 17,000 IU/mL to about 19,000 IU/mL, about 17,000 IU/mL to about 20,000 IU/mL, about 18,000 IU/mL to about 19,000 IU/mL, about 18,000 IU/mL to about 20,000 IU/mL, or about 19,000 IU/mL to about 20,000 IU/mL.

7. The method according to any one of embodiments 1-6, wherein the amount of the hyaluronidase administered is at least 15 IU, at least 25 IU, at least 50 IU, at least 100 IU, at least 200 IU, at least 300 IU, at least 450 IU, at least 600 IU, at least 900 IU, at least 1,000 IU, at least 1,250 IU, at least 1,500 IU, at least 1,750 IU, at least 2,000 IU, at least 3,000 IU, at least 4,000 IU, at least 5,000 IU, at least 6,000 IU, at least 7,000 IU, at least 8,000 IU, at least 9,000 IU, or at least 10,000 IU; and/or in an amount of at most 15 IU, at most 25 IU, at most 50 IU, at most 100 IU, at most 200 IU, at most 300 IU, at most 450 IU, at most 600 IU, at most 900 IU, at most 1,000 IU, at most 1,250 IU, at most 1,500 IU, at most 1,750 IU, at most 2,000 IU, at most 3,000 IU, at most 4,000 IU, at most 5,000 IU, at most 6,000 IU, at most 7,000 IU, at most 8,000 IU, at most 9,000 IU, or at most 10,000 IU; or in an amount of about 15 IU to about 25 IU, about 15 IU to about 50 IU, about 15 IU to about 100 IU, about 15 IU to about 200 IU, about 15 IU to about 300 IU, about 15 IU to about 400 IU, about 15 IU to about 450 IU, about 15 IU to about 600 IU, about 15 IU to about 750 IU, about 15 IU to about 900 IU, about 25 IU to about 50 IU, about 25 IU to about 100 IU, about 25 IU to about 200 IU, about 25 IU to about 300 IU, about 25 IU to about 400 IU, about 25 IU to about 450 IU, about 25 IU to about 600 IU, about 25 IU to about 750 IU, about 25 IU to about 900 IU, about 50 IU to about 100 IU, about 50 IU to about 200 IU, about 50 IU to about 300 IU, about 50 IU to about 400 IU, about 50 IU to about 450 IU, about 50 IU to about 600 IU, about 50 IU to about 750 IU, about 50 IU to about 900 IU, about 100 IU to about 200 IU, about 100 IU to about 300 IU, about 100 IU to about 400 IU, about 100 IU to about 450 IU, about 100 IU to about 600 IU, about 100 IU to about 750 IU, about 100 IU to about 900 IU, about 200 IU to about 300 IU, about 200 IU to about 400 IU, about 200 IU to about 450 IU, about 200 IU to about 600 IU, about 200 IU to about 750 IU, about 200 IU to about 900 IU, about 300 IU to about 450 IU, about 300 IU to about 600 IU, about 300 IU to about 750 IU, about 300 IU to about 900 IU, about 450 IU to about 600 IU, about 450 IU to about 750 IU, about 450 IU to about 900 IU, about 450 IU to about 1,000 IU, about 450 IU to about 1,250 IU, about 600 IU to about 750 IU, about 600 IU to about 900 IU, about 600 IU to about 1,000 IU, about 600 IU to about 1,250 IU, about 600 IU to about 1,500 IU, about 750 IU to about 900 IU, about 750 IU to about 1,000 IU, about 750 IU to about 1,250 IU, about 750 IU to about 1,500 IU, about 750 IU to about 1,750 IU, about 900 IU to about 1,000 IU, about 900 IU to about 1,250 IU, about 900 IU to about 1,500 IU, about 900 IU to about 1,750 IU, about 900 IU to about 2,000 IU, about 1,000 IU to about 1,250 IU, about 1,000 IU to about 1,500 IU, about 1,000 IU to about 1,750 IU, about 1,000 IU to about 2,000 IU, about 1,000 IU to about 3,000 IU, about 1,000 IU to about 4,000 IU, about 1,000 IU to about 5,000 IU, about 1,000 IU to about 6,000 IU, about 1,000 IU to about 7,000 IU, about 1,000 IU to about 8,000 IU, about 1,000 IU to about 9,000 IU, about 1,000 IU to about 10,000 IU, about 2,000 IU to about 3,000 IU, about 2,000 IU to about 4,000 IU, about 2,000 IU to about 5,000 IU, about 2,000 IU to about 6,000 IU, about 2,000 IU to about 7,000 IU, about 2,000 IU to about 8,000 IU, about 2,000 IU to about 9,000 IU, about 2,000 IU to about 10,000 IU, about 2,500 IU to about 3,000 IU, about 2,500 IU to about 4,000 IU, about 2,500 IU to about 5,000 IU, about 2,500 IU to about 6,000 IU, about 2,500 IU to about 7,000 IU, about 2,500 IU to about 8,000 IU, about 2,500 IU to about 9,000 IU, about 2,500 IU to about 10,000 IU, about 3,000 IU to about 4,000 IU, about 3,000 IU to about 5,000 IU, about 3,000 IU to about 6,000 IU, about 3,000 IU to about 7,000 IU, about 3,000 IU to about 8,000 IU, about 3,000 IU to about 9,000 IU, about 3,000 IU to about 10,000 IU, about 4,000 IU to about 5,000 IU, about 4,000 IU to about 6,000 IU, about 4,000 IU to about 7,000 IU, about 4,000 IU to about 8,000 IU, about 4,000 IU to about 9,000 IU, about 4,000 IU to about 10,000 IU, about 5,000 IU to about 6,000 IU, about 5,000 IU to about 7,000 IU, about 5,000 IU to about 8,000 IU, about 5,000 IU to about 9,000 IU, about 5,000 IU to about 10,000 IU, about 6,000 IU to about 7,000 IU, about 6,000 IU to about 8,000 IU, about 6,000 IU to about 9,000 IU, about 6,000 IU to about 10,000 IU, about 7,000 IU to about 8,000 IU, about 7,000 IU to about 9,000 IU, about 7,000 IU to about 10,000 IU, about 8,000 IU to about 9,000 IU, about 8,000 IU to about 10,000 IU, or about 9,000 IU to about 10,000 IU.

8. The method according to any one of embodiments 1-7, wherein the composition is administered as a single dose or in multiple doses.

9. The method according to any one of embodiments 1-8, wherein the composition is administered in a volume of at least 5 μL, at least 10 μL, at least 20 μL, at least 30 μL, at least 40 μL, at least 50 μL, at least 75 μL, at least 100 μL, at least 200 μL, at least 300 μL, at least 400 μL, or at least 500 μL; and/or in a volume of at most 5 μL, at most 10 μL, at most 20 μL, at most 30 μL, at most 40 μL, at most 50 μL, at most 75 μL, at most 100 μL, at most 200 μL, at most 300 μL, at most 400 μL, or at most 500 μL; or in a volume of about 5 μL to about 25 μL, about 5 μL to about 50 μL, about 5 μL to about 75 μL, about 5 μL to about 100 μL, about 10 μL to about 25 μL, about 10 μL to about 50 μL, about 10 μL to about 75 μL, about 10 μL to about 100 μL, about 25 μL to about 50 μL, about 25 μL to about 75 μL, about 25 μL to about 100 μL, about 25 μL to about 150 μL, about 50 μL to about 75 μL, about 50 μL to about 100 μL, about 50 μL to about 150 μL, about 50 μL to about 200 μL, about 50 μL to about 250 μL, about 100 μL to about 150 μL, about 100 μL to about 200 μL, about 100 μL to about 250 μL, about 100 μL to about 300 μL, about 100 μL to about 400 μL, about 100 μL to about 500 μL, about 200 μL to about 300 μL, about 200 μL to about 400 μL, about 200 μL to about 500 μL, about 300 μL to about 400 μL, about 300 μL to about 500 μL, or about 400 μL to about 500 μL.

10. The method according to any one of embodiments 1-9, wherein the composition enters a suprachoroidal space in at most 1 minute, at most 2 minutes, at most 3 minutes, at most 4 minutes, at most 5 minutes, at most 10 minutes, at most 15 minutes, at most 30 minutes, at most 45 minutes, at most 60 minutes, at most 75 minutes or at most 90 minutes; or in about 1 minute to about 3 minutes, about 1 minute to about 5 minutes, about 1 minute to about 7 minutes, about 1 minute to about 10 minutes, about 1 minute to about 15 minutes, about 3 minutes to about 5 minutes, about 3 minutes to about 7 minutes, about 3 minutes to about 10 minutes, about 3 minutes to about 15 minutes, about 5 minutes to about 7 minutes, about 5 minutes to about 10 minutes, about 5 minutes to about 15 minutes, about 5 minutes to about 30 minutes, about 10 minutes to about 15 minutes, about 10 minutes to about 30 minutes, about 15 minutes to about 30 minutes, about 15 minutes to about 45 minutes, about 15 minutes to about 60 minutes, about 15 minutes to about 75 minutes, about 15 minutes to about 90 minutes.

11. The method according to any one of embodiments 1-10, wherein the hyaluronic acid-induced blockage in the one or more blood vessels supplying blood to the eye is reduced or eliminated in at most 1 minute, at most 2 minutes, at most 3 minutes, at most 4 minutes, at most 5 minutes, at most 10 minutes, or at most 15 minutes, at most 30 minutes, at most 45 minutes, at most 60 minutes, at most 75 minutes or at most 90 minutes; or in about 1 minute to about 3 minutes, about 1 minute to about 5 minutes, about 1 minute to about 7 minutes, about 1 minute to about 10 minutes, about 1 minute to about 15 minutes, about 3 minutes to about 5 minutes, about 3 minutes to about 7 minutes, about 3 minutes to about 10 minutes, about 3 minutes to about 15 minutes, about 5 minutes to about 7 minutes, about 5 minutes to about 10 minutes, about 5 minutes to about 15 minutes, about 5 minutes to about 30 minutes, about 10 minutes to about 15 minutes, about 10 minutes to about 30 minutes, about 15 minutes to about 30 minutes, about 15 minutes to about 45 minutes, about 15 minutes to about 60 minutes, about 15 minutes to about 75 minutes, about 15 minutes to about 90 minutes.

12. A composition comprising a hyaluronidase for use in reducing or eliminating a hyaluronic acid-induced blockage in the one or more blood vessels supplying blood to the eye.

13. Use of a composition comprising a hyaluronidase for reducing or eliminating a hyaluronic acid-induced blockage in the one or more blood vessels supplying blood to the eye.

14. A composition comprising a hyaluronidase for use in the manufacture of a medicament for reducing or eliminating a hyaluronic acid-induced blockage in the one or more blood vessels supplying blood to the eye.

15. The use according to any one of embodiments 12-14, wherein the composition is administered using a delivery system.

16. A delivery system comprising a composition including a hyaluronidase for use in reducing or eliminating a hyaluronic acid-induced blockage in the one or more blood vessels supplying blood to the eye.

17. Use of a delivery system comprising a composition including a hyaluronidase for reducing or eliminating a hyaluronic acid-induced blockage in the one or more blood vessels supplying blood to the eye.

18. A composition comprising a hyaluronidase for use in the manufacture of a medicament for reducing or eliminating a hyaluronic acid-induced blockage in the one or more blood vessels supplying blood to the eye, wherein the composition is contained in a delivery system.

19. The use according to any one of embodiments 12-18, wherein the composition is administered to a suprachoroidal space of the eye.

20. The method according to any one of embodiments 12-19, wherein the composition comprises the hyaluronidase in a concentration of at least 15 IU/mL, at least 25 IU/mL, at least 50 IU/mL, at least 100 IU/mL, at least 200 IU/mL, at least 300 IU/mL, at least 450 IU/mL, at least 600 IU/mL, at least 900 IU/mL, at least 1,000 IU/mL, at least 1,250 IU/mL, at least 1,500 IU/mL, at least 1,750 IU/mL, at least 2,000 IU/mL, at least 3,000 IU/mL, at least 4,000 IU/mL, at least 5,000 IU/mL, at least 6,000 IU/mL, at least 7,000 IU/mL, at least 8,000 IU/mL, at least 9,000 IU/mL, at least 10,000 IU/mL, at least 11,000 IU/mL, at least 12,000 IU/mL, at least 13,000 IU/mL, at least 14,000 IU/mL, at least 15,000 IU/mL, at least 16,000 IU/mL, at least 17,000 IU/mL, at least 18,000 IU/mL, at least 19,000 IU/mL, or at least 20,000 IU/mL; and/or in an amount of at most 15 IU/mL, at most 25 IU/mL, at most 50 IU/mL, at most 100 IU/mL, at most 200 IU/mL, at most 300 IU/mL, at most 450 IU/mL, at most 600 IU/mL, at most 900 IU/mL, at most 1,000 IU/mL, at most 1,250 IU/mL, at most 1,500 IU/mL, at most 1,750 IU/mL, at most 2,000 IU/mL, at most 3,000 IU/mL, at most 4,000 IU/mL, at most 5,000 IU/mL, at most 6,000 IU/mL, at most 7,000 IU/mL, at most 8,000 IU/mL, at most 9,000 IU/mL, at most 10,000 IU/mL, at most 11,000 IU/mL, at most 12,000 IU/mL, at most 13,000 IU/mL, at most 14,000 IU/mL, at most 15,000 IU/mL, at most 16,000 IU/mL, at most 17,000 IU/mL, at most 18,000 IU/mL, at most 19,000 IU/mL, or at most 20,000 IU/mL; or in an amount of about 15 IU/mL to about 25 IU/mL, about 15 IU/mL to about 50 IU/mL, about 15 IU/mL to about 100 IU/mL, about 15 IU/mL to about 200 IU/mL, about 15 IU/mL to about 300 IU/mL, about 15 IU/mL to about 400 IU/mL, about 15 IU/mL to about 450 IU/mL, about 15 IU/mL to about 600 IU/mL, about 15 IU/mL to about 750 IU/mL, about 15 IU/mL to about 900 IU/mL, about 25 IU/mL to about 50 IU/mL, about 25 IU/mL to about 100 IU/mL, about 25 IU/mL to about 200 IU/mL, about 25 IU/mL to about 300 IU/mL, about 25 IU/mL to about 400 IU/mL, about 25 IU/mL to about 450 IU/mL, about 25 IU/mL to about 600 IU/mL, about 25 IU/mL to about 750 IU/mL, about 25 IU/mL to about 900 IU/mL, about 50 IU/mL to about 100 IU/mL, about 50 IU/mL to about 200 IU/mL, about 50 IU/mL to about 300 IU/mL, about 50 IU/mL to about 400 IU/mL, about 50 IU/mL to about 450 IU/mL, about 50 IU/mL to about 600 IU/mL, about 50 IU/mL to about 750 IU/mL, about 50 IU/mL to about 900 IU/mL, about 100 IU/mL to about 200 IU/mL, about 100 IU/mL to about 300 IU/mL, about 100 IU/mL to about 400 IU/mL, about 100 IU/mL to about 450 IU/mL, about 100 IU/mL to about 600 IU/mL, about 100 IU/mL to about 750 IU/mL, about 100 IU/mL to about 900 IU/mL, about 200 IU/mL to about 300 IU/mL, about 200 IU/mL to about 400 IU/mL, about 200 IU/mL to about 450 IU/mL, about 200 IU/mL to about 600 IU/mL, about 200 IU/mL to about 750 IU/mL, about 200 IU/mL to about 900 IU/mL, about 300 IU/mL to about 450 IU/mL, about 300 IU/mL to about 600 IU/mL, about 300 IU/mL to about 750 IU/mL, about 300 IU/mL to about 900 IU/mL, about 450 IU/mL to about 600 IU/mL, about 450 IU/mL to about 750 IU/mL, about 450 IU/mL to about 900 IU/mL, about 450 IU/mL to about 1,000 IU/mL, about 450 IU/mL to about 1,250 IU/mL, about 600 IU/mL to about 750 IU/mL, about 600 IU/mL to about 900 IU/mL, about 600 IU/mL to about 1,000 IU/mL, about 600 IU/mL to about 1,250 IU/mL, about 600 IU/mL to about 1,500 IU/mL, about 750 IU/mL to about 900 IU/mL, about 750 IU/mL to about 1,000 IU/mL, about 750 IU/mL to about 1,250 IU/mL, about 750 IU/mL to about 1,500 IU/mL, about 750 IU/mL to about 1,750 IU/mL, about 900 IU/mL to about 1,000 IU/mL, about 900 IU/mL to about 1,250 IU/mL, about 900 IU/mL to about 1,500 IU/mL, about 900 IU/mL to about 1,750 IU/mL, about 900 IU/mL to about 2,000 IU/mL, about 1,000 IU/mL to about 1,250 IU/mL, about 1,000 IU/mL to about 1,500 IU/mL, about 1,000 IU/mL to about 1,750 IU/mL, about 1,000 IU/mL to about 2,000 IU/mL, about 1,000 IU/mL to about 3,000 IU/mL, about 1,000 IU/mL to about 4,000 IU/mL, about 1,000 IU/mL to about 5,000 IU/mL, about 1,000 IU/mL to about 6,000 IU/mL, about 1,000 IU/mL to about 7,000 IU/mL, about 1,000 IU/mL to about 8,000 IU/mL, about 1,000 IU/mL to about 9,000 IU/mL, about 1,000 IU/mL to about 10,000 IU/mL, about 2,000 IU/mL to about 3,000 IU/mL, about 2,000 IU/mL to about 4,000 IU/mL, about 2,000 IU/mL to about 5,000 IU/mL, about 2,000 IU/mL to about 6,000 IU/mL, about 2,000 IU/mL to about 7,000 IU/mL, about 2,000 IU/mL to about 8,000 IU/mL, about 2,000 IU/mL to about 9,000 IU/mL, about 2,000 IU/mL to about 10,000 IU/mL, about 2,500 IU/mL to about 3,000 IU/mL, about 2,500 IU/mL to about 4,000 IU/mL, about 2,500 IU/mL to about 5,000 IU/mL, about 2,500 IU/mL to about 6,000 IU/mL, about 2,500 IU/mL to about 7,000 IU/mL, about 2,500 IU/mL to about 8,000 IU/mL, about 2,500 IU/mL to about 9,000 IU/mL, about 2,500 IU/mL to about 10,000 IU/mL, about 3,000 IU/mL to about 4,000 IU/mL, about 3,000 IU/mL to about 5,000 IU/mL, about 3,000 IU/mL to about 6,000 IU/mL, about 3,000 IU/mL to about 7,000 IU/mL, about 3,000 IU/mL to about 8,000 IU/mL, about 3,000 IU/mL to about 9,000 IU/mL, about 3,000 IU/mL to about 10,000 IU/mL, about 4,000 IU/mL to about 5,000 IU/mL, about 4,000 IU/mL to about 6,000 IU/mL, about 4,000 IU/mL to about 7,000 IU/mL, about 4,000 IU/mL to about 8,000 IU/mL, about 4,000 IU/mL to about 9,000 IU/mL, about 4,000 IU/mL to about 10,000 IU/mL, about 5,000 IU/mL to about 6,000 IU/mL, about 5,000 IU/mL to about 7,000 IU/mL, about 5,000 IU/mL to about 8,000 IU/mL, about 5,000 IU/mL to about 9,000 IU/mL, about 5,000 IU/mL to about 10,000 IU/mL, about 6,000 IU/mL to about 7,000 IU/mL, about 6,000 IU/mL to about 8,000 IU/mL, about 6,000 IU/mL to about 9,000 IU/mL, about 6,000 IU/mL to about 10,000 IU/mL, about 7,000 IU/mL to about 8,000 IU/mL, about 7,000 IU/mL to about 9,000 IU/mL, about 7,000 IU/mL to about 10,000 IU/mL, about 8,000 IU/mL to about 9,000 IU/mL, about 8,000 IU/mL to about 10,000 IU/mL, about 9,000 IU/mL to about 10,000 IU/mL, about 10,000 IU/mL to about 11,000 IU/mL, about 10,000 IU/mL to about 12,000 IU/mL, about 10,000 IU/mL to about 13,000 IU/mL, about 10,000 IU/mL to about 14,000 IU/mL, about 10,000 IU/mL to about 15,000 IU/mL, about 10,000 IU/mL to about 16,000 IU/mL, about 10,000 IU/mL to about 17,000 IU/mL, about 10,000 IU/mL to about 18,000 IU/mL, about 10,000 IU/mL to about 19,000 IU/mL, about 10,000 IU/mL to about 20,000 IU/mL, about 11,000 IU/mL to about 12,000 IU/mL, about 11,000 IU/mL to about 13,000 IU/mL, about 11,000 IU/mL to about 14,000 IU/mL, about 11,000 IU/mL to about 15,000 IU/mL, about 11,000 IU/mL to about 16,000 IU/mL, about 11,000 IU/mL to about 17,000 IU/mL, about 11,000 IU/mL to about 18,000 IU/mL, about 11,000 IU/mL to about 19,000 IU/mL, about 11,000 IU/mL to about 20,000 IU/mL, about 12,000 IU/mL to about 13,000 IU/mL, about 12,000 IU/mL to about 14,000 IU/mL, about 12,000 IU/mL to about 15,000 IU/mL, about 12,000 IU/mL to about 16,000 IU/mL, about 12,000 IU/mL to about 17,000 IU/mL, about 12,000 IU/mL to about 18,000 IU/mL, about 12,000 IU/mL to about 19,000 IU/mL, about 12,000 IU/mL to about 20,000 IU/mL, about 13,000 IU/mL to about 14,000 IU/mL, about 13,000 IU/mL to about 15,000 IU/mL, about 13,000 IU/mL to about 16,000 IU/mL, about 13,000 IU/mL to about 17,000 IU/mL, about 13,000 IU/mL to about 18,000 IU/mL, about 13,000 IU/mL to about 19,000 IU/mL, about 13,000 IU/mL to about 20,000 IU/mL, about 14,000 IU/mL to about 15,000 IU/mL, about 14,000 IU/mL to about 16,000 IU/mL, about 14,000 IU/mL to about 17,000 IU/mL, about 14,000 IU/mL to about 18,000 IU/mL, about 14,000 IU/mL to about 19,000 IU/mL, about 14,000 IU/mL to about 20,000 IU/mL, about 15,000 IU/mL to about 16,000 IU/mL, about 15,000 IU/mL to about 17,000 IU/mL, about 15,000 IU/mL to about 18,000 IU/mL, about 15,000 IU/mL to about 19,000 IU/mL, about 15,000 IU/mL to about 20,000 IU/mL, about 16,000 IU/mL to about 17,000 IU/mL, about 16,000 IU/mL to about 18,000 IU/mL, about 16,000 IU/mL to about 19,000 IU/mL, about 16,000 IU/mL to about 20,000 IU/mL, about 17,000 IU/mL to about 18,000 IU/mL, about 17,000 IU/mL to about 19,000 IU/mL, about 17,000 IU/mL to about 20,000 IU/mL, about 18,000 IU/mL to about 19,000 IU/mL, about 18,000 IU/mL to about 20,000 IU/mL, or about 19,000 IU/mL to about 20,000 IU/mL.

21. The use according to any one of embodiments 12-20, wherein the amount of hyaluronidase administered is at least 15 IU, at least 25 IU, at least 50 IU, at least 100 IU, at least 200 IU, at least 300 IU, at least 450 IU, at least 600 IU, at least 900 IU, at least 1,000 IU, at least 1,250 IU, at least 1,500 IU, at least 1,750 IU, at least 2,000 IU, at least 3,000 IU, at least 4,000 IU, or at least 5,000 IU; and/or in an amount of at most 15 IU, at most 25 IU, at most 50 IU, at most 100 IU, at most 200 IU, at most 300 IU, at most 450 IU, at most 600 IU, at most 900 IU, at most 1,000 IU, at most 1,250 IU, at most 1,500 IU, at most 1,750 IU, at most 2,000 IU, at most 3,000 IU, at most 4,000 IU, or at most 5,000 IU; or in an amount of about 15 IU to about 25 IU, about 15 IU to about 50 IU, about 15 IU to about 100 IU, about 15 IU to about 200 IU, about 15 IU to about 300 IU, about 15 IU to about 400 IU, about 15 IU to about 450 IU, about 15 IU to about 600 IU, about 15 IU to about 750 IU, about 15 IU to about 900 IU, about 25 IU to about 50 IU, about 25 IU to about 100 IU, about 25 IU to about 200 IU, about 25 IU to about 300 IU, about 25 IU to about 400 IU, about 25 IU to about 450 IU, about 25 IU to about 600 IU, about 25 IU to about 750 IU, about 25 IU to about 900 IU, about 50 IU to about 100 IU, about 50 IU to about 200 IU, about 50 IU to about 300 IU, about 50 IU to about 450 IU, about 50 IU to about 600 IU, about 50 IU to about 750 IU, about 50 IU to about 900 IU, about 100 IU to about 200 IU, about 100 IU to about 300 IU, about 100 IU to about 450 IU, about 100 IU to about 600 IU, about 100 IU to about 750 IU, about 100 IU to about 900 IU, about 200 IU to about 300 IU, about 200 IU to about 450 IU, about 200 IU to about 600 IU, about 200 IU to about 750 IU, about 200 IU to about 900 IU, about 300 IU to about 450 IU, about 300 IU to about 600 IU, about 300 IU to about 750 IU, about 300 IU to about 900 IU, about 450 IU to about 600 IU, about 450 IU to about 750 IU, about 450 IU to about 900 IU, about 450 IU to about 1,000 IU, about 450 IU to about 1,250 IU, about 600 IU to about 750 IU, about 600 IU to about 900 IU, about 600 IU to about 1,000 IU, about 600 IU to about 1,250 IU, about 600 IU to about 1,500 IU, about 750 IU to about 900 IU, about 750 IU to about 1,000 IU, about 750 IU to about 1,250 IU, about 750 IU to about 1,500 IU, about 750 IU to about 1,750 IU, about 900 IU to about 1,000 IU, about 900 IU to about 1,250 IU, about 900 IU to about 1,500 IU, about 900 IU to about 1,750 IU, about 900 IU to about 2,000 IU, about 1,000 IU to about 1,250 IU, about 1,000 IU to about 1,500 IU, about 1,000 IU to about 1,750 IU, about 1,000 IU to about 2,000 IU, about 1,000 IU to about 3,000 IU, about 1,000 IU to about 4,000 IU, about 1,000 IU to about 5,000 IU, about 2,000 IU to about 3,000 IU, about 2,000 IU to about 4,000 IU, about 2,000 IU to about 5,000 IU, about 2,500 IU to about 3,000 IU, about 2,500 IU to about 4,000 IU, about 2,500 IU to about 5,000 IU, about 3,000 IU to about 4,000 IU, about 3,000 IU to about 5,000 IU, or about 4,000 IU to about 5,000 IU.

22. The method according to any one of embodiments 12-21, wherein the composition is administered as a single dose or in multiple doses.

23. The use according to any one of embodiments 12-22, wherein the composition or medicament is administered in a volume of at least 5 µL, at least 10 µL, at least 20 µL, at least 30 µL, at least 40 µL, at least 50 µL, at least 75 µL, at least 100 µL, at least 200 µL, at least 300 µL, at least 400 µL, or at least 500 µL; and/or in a volume of at most 5 µL, at most 10 µL, at most 20 µL, at most 30 µL, at most 40 µL, at most 50 µL, at most 75 µL, at most 100 µL, at most 200 µL, at most 300 µL, at most 400 µL, or at most 500 µL; or in a volume of about 5 µL to about 25 µL, about 5 µL to about 50 µL, about 5 µL to about 75 µL, about 5 µL to about 100 µL, about 10 µL to about 25 µL, about 10 µL to about 50 µL, about 10 µL to about 75 µL, about 10 µL to about 100 µL, about 25 µL to about 50 µL, about 25 µL to about 75 µL, about 25 µL to about 100 µL, about 25 µL to about 150 µL, about 50 µL to about 75 µL, about 50 µL to about 100 µL, about 50 µL to about 150 µL, about 50 µL to about 200 µL, about 50 µL to about 250 µL, about 100 µL to about 150 µL, about 100 µL to about 200 µL, about 100 µL to about 250 µL, about 100 µL to about 300 µL, about 100 µL to about 400 µL, about 100 µL to about 500 µL, about 200 µL to about 300 µL, about 200 µL to about 400 µL, about 200 µL to about 500 µL, about 300 µL to about 400 µL, about 300 µL to about 500 µL, or about 400 µL to about 500 µL.

24. The use according to any one of embodiments 20-23, wherein the composition or medicament enters a suprachoroidal space in at most 1 minute, at most 2 minutes, at most 3 minutes, at most 4 minutes, at most 5 minutes, at most 10 minutes, at most 15 minutes, at most 30 minutes, at most 45 minutes, at most 60 minutes, at most 75 minutes or at most 90 minutes; or in about 1 minute to about 3 minutes, about 1 minute to about 5 minutes, about 1 minute to about 7 minutes, about 1 minute to about 10 minutes, about 1 minute to about 15 minutes, about 3 minutes to about 5 minutes, about 3 minutes to about 7 minutes, about 3 minutes to about 10 minutes, about 3 minutes to about 15 minutes, about 5 minutes to about 7 minutes, about 5 minutes to about 10 minutes, about 5 minutes to about 15 minutes, about 5 minutes to about 30 minutes, about 10 minutes to about 15 minutes, about 10 minutes to about 30 minutes, about 15 minutes to about 30 minutes, about 15 minutes to about 45 minutes, about 15 minutes to about 60 minutes, about 15 minutes to about 75 minutes, about 15 minutes to about 90 minutes.

25. The use according to any one of embodiments 12-24, wherein the hyaluronic acid-induced blockage in the one or more blood vessels supplying blood to the eye is reduced or eliminated in at most 1 minute, at most 2 minutes, at most 3 minutes, at most 4 minutes, at most 5 minutes, at most 10 minutes, at most 15 minutes, at most 30 minutes, at most 45 minutes, at most 60 minutes, at most 75 minutes or at most 90 minutes; or in about 1 minute to about 3 minutes, about 1 minute to about 5 minutes, about 1 minute to about 7 minutes, about 1 minute to about 10 minutes, about 1 minute to about 15 minutes, about 3 minutes to about 5 minutes, about 3 minutes to about 7 minutes, about 3 minutes to about 10 minutes, about 3 minutes to about 15 minutes, about 5 minutes to about 7 minutes, about 5 minutes to about 10 minutes, about 5 minutes to about 15 minutes, about 5 minutes to about 30 minutes, about 10 minutes to about 15 minutes, about 10 minutes to about 30 minutes, about 15 minutes to about 30 minutes, about 15 minutes to about 45 minutes, about 15 minutes to about 60 minutes, about 15 minutes to about 75 minutes, about 15 minutes to about 90 minutes.

26. A kit comprising one or more containers, each container including a pharmaceutical composition including a hyaluronidase.

27. The kit according to embodiment 26, wherein the pharmaceutical composition is in a liquid formulation.

28. The kit according to embodiment 26, wherein the pharmaceutical composition is in a dried formulation.

29. The kit according to any one of embodiments 26-28, wherein the one or more containers are each a delivery system.

30. The kit according to any one of embodiments 26-28, further comprising a delivery system.

31. The kit according to any one of embodiments 26-30, further comprising another container including a solvent.

32. The kit according to any one of embodiments 26-31, further comprising instructions.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, pharmaceutical compositions, or methods and uses disclosed herein.

Example 1

Rabbit Model of Filler-Induced Vascular Occlusion

In this example, New Zealand white rabbits were used to simulate hyaluronic acid polymer associated vascular occlusive loss of vision. These animals were selected due to the similarity of their ocular vascular anatomy to that of humans.

New Zealand white rabbits weighing 2.0 to 3.0 kg were acclimated to the study environment for a minimum of 1 week prior to the beginning of the study. At the completion of the acclimation period, each animal was physically examined for determination of suitability for the study including examination of the skin and external ears, eyes, abdomen, neurological, behavior, and general body condition. Animals determined to be in good health were released to the study. Released animals were allocated to four group of 3 animals each with each animal uniquely identified by a cage card number.

On the day of the surgical procedure (Day 0), all animals were anesthetized and dosed with an antibiotic. Each animal then underwent a surgical procedure to expose the expose the right carotid artery in the animal's neck. Using a 25-gauge or smaller needle attached to a syringe, 0.5 mL to 0.7 mL of a hyaluronic acid dermal filler was injected in the cranial direction into the right carotid artery over a minimum of 60 seconds. Once administration of the dermal filler was completed, the surgical incision site in the animal's neck was sutured closed. Approximately 5 minutes post-dermal filler administration, an eyelid speculum was positioned on the right eye of animals who then underwent one of four treatment protocols. Group 1 animals were injection controls that received no further treatment. Group 2-3 animals were each administered a composition by suprachoroidal injection using a 30-gauge needle in the inferior nasal quadrant of the right eye with Group 2 animals receiving 0.1 mL of Phospho-buffered saline (PBS)(control composition), and Group 3 animals receiving 0.1 mL of a hyaluronidase (2,400 IU/mL). Animals were allowed to recover normally from the anesthetic procedure. The left eye in all animals was untreated and served as a control in these experiments.

To assess visual activity, both optical coherence tomography angiography (OCT-A) and electroretinography (ERG) were performed. OCT-A is a non-contact retinal imaging system that uses infrared light to image retinal vasculature and determine vascular flow changes over time. In this study, each animal underwent OCT-A analysis to evaluate 1) pre-induction Day 0 versus post-induction Day 0 vascular flow changes; 2) pre-induction Day 0 versus post-induction Day 3 vascular flow changes; and 3) post-induction Day 0 versus post-induction Day 3 vascular flow changes. Full-field ERG was performed on both eyes of each animal on pre-induction Day 0 to obtain a baseline reading and on post-induction Day 3. Animals were dark adapted for at least 1 hour prior to ERG analysis. ERGs were elicited by brief flashes at 0.33 Hz delivered with a mini-ganzfeld photo-stimulator (Roland Instruments, Wiesbaden, Germany) at maximal intensity. Twenty responses were amplified, filtered, and averaged (Retiport Electrophysiologic Diagnostic Systems, Roland Instruments, Wiesbaden, Germany) for each animal. Animals underwent standard ERG measurements as dictated by ISCEV standards, including scotopic (0.01 candela), scotopic (3 candela), and photopic (3 candela) measurements. a-wave and b-wave ERG analysis was conducted to determine a-wave and b-wave amplitude changes over time, comparing pre-induction Day 0 (baseline) versus post-induction Day 3 under scotopic and photopic conditions.

At pre-induction Day 0, the right eye of Group 1 animals exhibited normal blood flow to the retina based on OCT-A analysis (Table 1) as well as normal neuronal activity in the retina based on ERG readings (Table 2). However, post-induction Day 3, all animals showed significantly reduced blood flow to the retina and ERG readings that were flat or essentially flat in the right eye (Tables 1 and 2) indicating a significant loss of blood flow and neuronal activity in the retina. As expected, the left eye of these animals showed normal blood flow and neuronal activity in the retina (Tables 1 and 2). Similarly, the right eye of Group 2 animals exhibited normal blood flow to the retina based on OCT-A analysis (Table 1) as well as normal neuronal activity in the retina based on ERG readings (Table 2). However, post-induction Day 3, all animals showed significantly reduced blood flow to the retina and ERG readings that were flat or essentially flat in the right eye (Tables 1 and 2) indicating a significant loss of blood flow and neuronal activity in the retina. As expected, the left eye of these animals showed normal blood flow and neuronal activity in the retina (Tables 1 and 2). As both Group 1 and Group 2 animals were controls, these results demonstrate that hyaluronic acid polymers can occlude blood flow to the retina and cause loss of retinal function and serve as a good model for hyaluronic acid polymer associated vascular occlusive loss of vision.

TABLE 1

Assessment of Blood Flow in Retina by OCT-A Analysis

| Animal | Pre-induction Day 0 | | Post-induction Day 3 | |
| --- | --- | --- | --- | --- |
| | Left Eye | Right Eye | Left Eye | Right Eye |
| Group 1-1 | +++ | +++ | +++ | − |
| Group 1-2 | +++ | +++ | +++ | − |
| Group 1-3 | +++ | +++ | +++ | − |
| Group 2-1 | +++ | +++ | +++ | − |
| Group 2-2 | +++ | +++ | +++ | − |
| Group 2-3 | +++ | +++ | +++ | − |
| Group 3-1 | +++ | +++ | +++ | +++ |
| Group 3-2 | +++ | +++ | +++ | + |
| Group 3-3 | +++ | +++ | +++ | ++ |
| Group 3-4 | +++ | +++ | +++ | + |

+++ Normal blood flow measured in retina.
++ Near-normal blood flow measured in retina.
+ Low but significant blood flow measured in retina.
− No appreciable blood flow measured retina.

TABLE 2

Assessment of Neuronal Activity in Retina by ERG Analysis

| Animal | Pre-induction Day 0 | | Post-induction Day 3 | |
| --- | --- | --- | --- | --- |
| | Left Eye | Right Eye | Left Eye | Right Eye |
| Group 1-1 | +++ | +++ | +++ | − |
| Group 1-2 | +++ | +++ | +++ | − |
| Group 1-3 | +++ | +++ | +++ | − |
| Group 2-1 | +++ | +++ | +++ | − |
| Group 2-2 | +++ | +++ | +++ | − |
| Group 2-3 | +++ | +++ | +++ | − |
| Group 3-1 | +++ | +++ | +++ | +++ |
| Group 3-2 | +++ | +++ | +++ | + |
| Group 3-3 | +++ | +++ | +++ | ++ |
| Group 3-4 | +++ | +++ | +++ | + |

+++ Normal neuronal activity measured in retina.
++ Near-normal neuronal activity measured in retina.
+ Low but significant neuronal activity measured in retina.
− No appreciable neuronal activity measured retina.

Analysis of Group 3 animals demonstrated that administration of hyaluronidase reversed hyaluronic acid polymer associated vascular occlusion in the retina. At pre-induction Day 0, the right eye of Group 3 animals exhibited normal blood flow to the retina based on OCT-A analysis (Table 1) as well as normal neuronal activity in the retina based on ERG readings (Table 2). These baseline measurements show that the animals in Group 3 exhibited functional neuronal activity. Surprisingly, post-induction Day 3, all animals also showed significant blood flow and neuronal activity in the retina (Tables 1 and 2). Although these levels were distinguishable from measurements obtained from the right eye on pre-induction Day 0 as well as measurements from the left eye control, the activity measured nonetheless illustrated a significant recovery from the vascular occlusion caused by the presence of hyaluronic acid polymers. These results demonstrate that hyaluronic acid polymers can occlude blood flow to the retina and cause loss of retinal function and serve as a good model for hyaluronic acid polymer associated vascular occlusive loss of vision. Furthermore, remarkably, small volumes of hyaluronidase administration into the suprachoroidal space cleared the hyaluronic acid dermal filler occlusion within the retinal circulation allowing for the reperfusion of the retinal tissue and reestablishment of neuronal activity Example 2

Rabbit Model of Filler-Induced Vascular Occlusion

New Zealand red rabbits will be used to simulate hyaluronic acid associated vascular occlusive loss of vision. These animals will be selected due to the similarity of their ocular vascular anatomy to that of humans. New Zealand white rabbits weighing 2.0 to 3.0 kg will be divided into groups based on the hyaluronidase dose and administration time.

Hyaluronic acid filler will be administered into the internal carotid artery of animals to create a central retinal artery occlusion. This artery occlusion as well as subsequent ischemia will be confirmed by both retinal fundus photography, OCT-A, and ERG analyses. Different doses of hyaluronidase will be suprachoroidally administered at several post-obstruction time points to assess both dose and timing effectiveness of the treatment. Control animals will be injected with hyaluronic acid filler in the same manner as experimental animals but will receive no hyaluronidase treatment. Fundus photography and electroretinogram changes will be recorded at 30, 60, 90, and 120 minutes after administration of hyaluronidase. Electroretinography will be performed after 60 and 120 minutes to confirm the retinal reperfusion and electrophysiologic function.

In one series of experiments, a central retinal artery occlusion will be induced by injecting 0.5 mL to 0.9 mL of hyaluronic acid filler into rabbits, which will be divided into four experimental groups each containing 2 or 3 animals with Group 1 animals receiving suprachoroidally administered 100 µL hyaluronidase (400 IU/mL) 5 minutes after hyaluronic acid filler injection; Group 2 animals receiving suprachoroidally administered 100 µL hyaluronidase (400 IU/mL) 10 minutes after hyaluronic acid filler injection; Group 3 animals receiving suprachoroidally administered 100 µL hyaluronidase (600 IU/mL) 5 minutes after hyaluronic acid filler injection; and Group 4 animals receiving suprachoroidally administered 100 µL hyaluronidase (650 IU/mL) 10 minutes after hyaluronic acid filler injection.

In another series of experiments, a central retinal artery occlusion will be induced by injecting 0.5 mL to 0.9 mL of hyaluronic acid filler into rabbits, which will be divided into four experimental groups each containing 2 or 3 animals with Group 1 animals receiving suprachoroidally administered 100 µL hyaluronidase (1,000 IU/mL) 5 minutes after hyaluronic acid filler injection; Group 2 animals receiving suprachoroidally administered 100 µL hyaluronidase (1,000 IU/mL) 10 minutes after hyaluronic acid filler injection; Group 3 animals receiving suprachoroidally administered 100 µL hyaluronidase (3,000 IU/mL) 5 minutes after hyaluronic acid filler injection; and Group 4 animals receiving suprachoroidally administered 100 µL hyaluronidase (3,000 IU/mL) 10 minutes after hyaluronic acid filler injection.

In another series of experiments, a central retinal artery occlusion will be induced by injecting 0.5 mL to 0.9 mL of hyaluronic acid filler into rabbits, which will be divided into four experimental groups each containing 2 or 3 animals with Group 1 animals receiving suprachoroidally administered 100 µL hyaluronidase (10,000 IU/mL) 5 minutes after hyaluronic acid filler injection; Group 2 animals receiving suprachoroidally administered 100 µL hyaluronidase (10,000 IU/mL) 10 minutes after hyaluronic acid filler injection; Group 3 animals receiving suprachoroidally administered 100 µL hyaluronidase (15,000 IU/mL) 5 minutes after hyaluronic acid filler injection; and Group 4 animals receiving suprachoroidally administered 100 µL hyaluronidase (15,000 IU/mL) 10 minutes after hyaluronic acid filler injection.

In another series of experiments, a central retinal artery occlusion will be induced by injecting 0.5 mL to 0.9 mL of hyaluronic acid filler into rabbits, which will be divided into four experimental groups each containing 2 or 3 animals with Group 1 animals receiving suprachoroidally administered 100 µL hyaluronidase (15,000 IU/mL) 5 minutes after hyaluronic acid filler injection; Group 2 animals receiving suprachoroidally administered 100 µL hyaluronidase (15,000 IU/mL) 10 minutes after hyaluronic acid filler injection; Group 3 animals receiving suprachoroidally administered 100 µL hyaluronidase (20,000 IU/mL) 5 minutes after hyaluronic acid filler injection; and Group 4 animals receiving suprachoroidally administered 100 µL hyaluronidase (20,000 IU/mL) 10 minutes after hyaluronic acid filler injection.

In another series of experiments, a central retinal artery occlusion will be induced by injecting 0.5 mL to 0.9 mL of hyaluronic acid filler into rabbits, which will be divided into four experimental groups each containing 2 or 3 animals with Group 1 animals receiving suprachoroidally administered 100 µL hyaluronidase (400 IU/mL) 15 minutes after hyaluronic acid filler injection; Group 2 animals receiving suprachoroidally administered 100 µL hyaluronidase (400 IU/mL) 30 minutes after hyaluronic acid filler injection; Group 3 animals receiving suprachoroidally administered 100 µL hyaluronidase (650 IU/mL) 15 minutes after hyaluronic acid filler injection; and Group 4 animals receiving suprachoroidally administered 100 µL hyaluronidase (650 IU/mL) 30 minutes after hyaluronic acid filler injection.

In another series of experiments, a central retinal artery occlusion will be induced by injecting 0.5 mL to 0.9 mL of hyaluronic acid filler into rabbits, which will be divided into four experimental groups each containing 2 or 3 animals with Group 1 animals receiving suprachoroidally administered 100 µL hyaluronidase (1,000 IU/mL) 15 minutes after hyaluronic acid filler injection; Group 2 animals receiving suprachoroidally administered 100 µL hyaluronidase (1,000 IU/mL) 30 minutes after hyaluronic acid filler injection; Group 3 animals receiving suprachoroidally administered 100 µL hyaluronidase (3.000 IU/mL) 15 minutes after hyaluronic acid filler injection; and Group 4 animals receiving suprachoroidally administered 100 µL hyaluronidase (3,000 IU/mL) 30 minutes after hyaluronic acid filler injection.

In another series of experiments, a central retinal artery occlusion will be induced by injecting 0.5 mL to 0.9 mL of hyaluronic acid filler into rabbits, which will be divided into four experimental groups each containing 2 or 3 animals with Group 1 animals receiving suprachoroidally administered 100 µL hyaluronidase (10,000 IU/mL) 15 minutes after hyaluronic acid filler injection; Group 2 animals receiving suprachoroidally administered 100 µL hyaluronidase (10,000 IU/mL) 30 minutes after hyaluronic acid filler injection; Group 3 animals receiving suprachoroidally administered 100 µL hyaluronidase (15,000 IU/mL) 15 minutes after hyaluronic acid filler injection; and Group 4 animals receiving suprachoroidally administered 100 µL hyaluronidase (15,000 IU/mL) 30 minutes after hyaluronic acid filler injection.

In another series of experiments, a central retinal artery occlusion will be induced by injecting 0.5 mL to 0.9 mL of hyaluronic acid filler into rabbits, which will be divided into four experimental groups each containing 2 or 3 animals with Group 1 animals receiving suprachoroidally administered 100 µL hyaluronidase (15,000 IU/mL) 15 minutes after hyaluronic acid filler injection; Group 2 animals receiving suprachoroidally administered 100 µL hyaluronidase (15,000 IU/mL) 30 minutes after hyaluronic acid filler injection; Group 3 animals receiving suprachoroidally administered 100 µL hyaluronidase (20,000 IU/mL) 15 minutes after hyaluronic acid filler injection; and Group 4 animals receiving suprachoroidally administered 100 µL hyaluronidase (20,000 IU/mL) 30 minutes after hyaluronic acid filler injection.

Analysis of eyes from experimental animals by retinal fundus photography, OCT-A, and ERG analysis are expected to reveal no significant central retinal artery occlusion or loss of visual acuity after hyaluronidase treatment. Control animals, on the other hand, are expected to exhibit no improvement in filler-induced central retinal artery occlusion or visual acuity, suggesting loss of vision.

In closing, foregoing descriptions of embodiments of the present invention have been presented for the purposes of illustration and description. It is to be understood that, although aspects of the present invention are highlighted by referring to specific embodiments, one skilled in the art will readily appreciate that these described embodiments are only illustrative of the principles comprising the present invention. As such, the specific embodiments are not intended to be exhaustive or to limit the invention to the precise forms disclosed. Therefore, it should be understood that embodiments of the disclosed subject matter are in no way limited to a particular element, compound, composition, component, article, apparatus, methodology, use, protocol, step, and/or limitation described herein, unless expressly stated as such.

In addition, groupings of alternative embodiments, elements, steps and/or limitations of the present invention are not to be construed as limitations. Each such grouping may be referred to and claimed individually or in any combination with other groupings disclosed herein. It is anticipated that one or more alternative embodiments, elements, steps and/or limitations of a grouping may be included in, or deleted from, the grouping for reasons of convenience and/or patentability. When any such inclusion or deletion occurs, the specification is deemed to contain the grouping as modified, thus fulfilling the written description of all Markush groups used in the appended claims.

Furthermore, those of ordinary skill in the art will recognize that certain changes, modifications, permutations, alterations, additions, subtractions and sub-combinations thereof can be made in accordance with the teachings herein without departing from the spirit of the present invention. Furthermore, it is intended that the following appended claims and claims hereafter introduced are interpreted to include all such changes, modifications, permutations, alterations, additions, subtractions and sub-combinations as are within their true spirit and scope. Accordingly, the scope of the present invention is not to be limited to that precisely as shown and described by this specification.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

The words, language, and terminology used in this specification is for the purpose of describing particular embodiments, elements, steps and/or limitations only and is not intended to limit the scope of the present invention, which is defined solely by the claims. In addition, such words, language, and terminology are to be understood not only in the sense of their commonly defined meanings, but to include by special definition in this specification structure, material or acts beyond the scope of the commonly defined meanings. Thus, if an element, step or limitation can be understood in the context of this specification as including more than one meaning, then its use in a claim must be understood as being generic to all possible meanings supported by the specification and by the word itself.

The definitions and meanings of the elements, steps or limitations recited in a claim set forth below are, therefore, defined in this specification to include not only the combination of elements, steps or limitations which are literally set forth, but all equivalent structure, material or acts for performing substantially the same function in substantially the same way to obtain substantially the same result. In this sense it is therefore contemplated that an equivalent substitution of two or more elements, steps or limitations may be made for any one of the elements, steps or limitations in a claim set forth below or that a single element, step or limitation may be substituted for two or more elements, steps or limitations in such a claim. Although elements, steps or limitations may be described above as acting in certain combinations and even initially claimed as such, it is to be expressly understood that one or more elements, steps or limitations from a claimed combination can in some cases be excised from the combination and that the claimed combination may be directed to a sub-combination or variation of a sub-combination. As such, notwithstanding the fact that the elements, steps and/or limitations of a claim are set forth below in a certain combination, it must be expressly understood that the invention includes other combinations of fewer, more or different elements, steps and/or limitations, which are disclosed in above even when not initially claimed in such combinations. Furthermore, insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. Accordingly, the claims are thus to be understood to include what is specifically illustrated and described above, what is conceptually equivalent, what can be obviously substituted and also what essentially incorporates the essential idea of the invention.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as, e.g., "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising", variations thereof such as, e.g., "comprise" and "comprises", and equivalent open-ended transitional phrases thereof like "including," "containing" and "having", encompass all the expressly recited elements, limitations, steps, integers, and/or features alone or in combination with unrecited subject matter; the named elements, limitations, steps, integers, and/or features are essential, but other unnamed elements, limitations, steps, integers, and/or features may be added and still form a construct within the scope of the claim. Specific embodiments disclosed herein may be further limited in the claims using the closed-ended transitional phrases "consisting of" or "consisting essentially of" (or variations thereof such as, e.g., "consist of", "consists of", "consist essentially of", and "consists essentially of") in lieu of or as an amendment for "comprising." When used in the claims, whether as filed or added per amendment, the closed-ended transitional phrase "consisting of" excludes any element, limitation, step, integer, or feature not expressly recited in the claims. The closed-ended transitional phrase "consisting essentially of" limits the scope of a claim to the expressly recited elements, limitations, steps, integers, and/or features and any other elements, limitations, steps, integers, and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps, integers, and/or features specifically recited in the claim, whereas the meaning of the closed-ended transitional phrase "consisting essentially of" is being defined as only including those elements, limitations, steps, integers, and/or features specifically recited in the claim and those elements, limitations, steps, integers, and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such, the embodiments described herein or so claimed with the phrase "comprising" expressly and unambiguously provide description, enablement, and support for the phrases "consisting essentially of" and "consisting of."

Lastly, all patents, patent publications, and other references cited and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard is or should be construed as an admission that the inventors are not entitled to antedate such disclosure by virtue of prior invention or for any other reason. All statements as to the date or representation as to the contents of these documents are based on the information available to the applicant and do not constitute any admission as to the correctness of the dates or contents of these documents.

The invention claimed is:

1. A method of reducing or eliminating a hyaluronic acid-induced blockage in one or more blood vessels supplying blood to an eye in an individual in need thereof, the method comprising administering at most 500 µL of a composition comprising a therapeutically effective amount of hyaluronidase of at least 6,000 IU/mL to a suprachoroidal space of the eye of the individual,
wherein administration of the hyaluronidase reduces or eliminates a hyaluronic acid-induced blockage in one or more blood vessels supplying blood to an eye in at most 30 minutes.

2. The method according to claim 1, wherein the therapeutically effective amount of hyaluronidase is in a concentration of at least 8,000 IU/mL.

3. The method according to claim 1, wherein the therapeutically effective amount of hyaluronidase is in a concentration of about 6,000 IU/mL to about 10,000 IU/mL.

4. The method according to claim 1, wherein the therapeutically effective amount of hyaluronidase is in a concentration of at least 10,000 IU/mL.

5. The method according to claim 1, wherein the therapeutically effective amount of hyaluronidase is in a concentration of at least 15,000 IU/mL.

6. The method according to claim 1, wherein the therapeutically effective amount of hyaluronidase is in a concentration of at least 20,000 IU/mL.

7. The method according to claim 1, wherein the composition is administered as a single dose or in multiple doses.

8. The method according to claim 1, wherein the composition is administered in a volume of about 50 µL to about 250 µL.

9. The method according to claim 1, wherein the composition enters a suprachoroidal space in at most 10 minutes.

10. The method according to claim 1, wherein the hyaluronic acid-induced blockage in the one or more blood vessels supplying blood to the eye is reduced or eliminated in at most 15 minutes.

11. A method of reducing or inhibiting a vascular occlusion in an eye of an individual in need thereof, the method comprising administering at most 400 µL of a composition comprising a therapeutically effective amount of hyaluronidase of at least 6,000 IU/mL to a suprachoroidal space of the eye of the individual,
wherein administration of the hyaluronidase reduces or eliminates a hyaluronic acid-induced blockage in one or more blood vessels supplying blood to an eye in at most 30 minutes, thereby reducing or inhibiting the vascular occlusion in the eye.

12. The method according to claim 11, wherein the therapeutically effective amount of hyaluronidase is in a concentration of at least 8,000 IU/mL.

13. The method according to claim 11, wherein the therapeutically effective amount of hyaluronidase is in a concentration of about 6,000 IU/mL to about 10,000 IU/mL.

14. The method according to claim 11, wherein the therapeutically effective amount of hyaluronidase is in a concentration of at least 10,000 IU/mL.

15. The method according to claim 11, wherein the therapeutically effective amount of hyaluronidase is in a concentration of at least 15,000 IU/mL.

16. The method according to claim 11, wherein the therapeutically effective amount of hyaluronidase is in a concentration of at least 20,000 IU/mL.

17. The method according to claim 11, wherein the composition is administered as a single dose or in multiple doses.

18. The method according to claim 11, wherein the composition is administered in a volume of about 50 µL to about 250 µL.

19. The method according to claim 11, wherein the composition enters a suprachoroidal space in at most 10 minutes.

20. The method according to claim 11, wherein the hyaluronic acid-induced blockage in the one or more blood vessels supplying blood to the eye is reduced or eliminated in at most 15 minutes.

* * * * *